(12) United States Patent
Murakami et al.

(10) Patent No.: US 9,956,343 B2
(45) Date of Patent: May 1, 2018

(54) PHARMACEUTICAL INJECTION DEVICE

(71) Applicant: Panasonic Healthcare Holdings Co., Ltd., Minato-ku, Tokyo (JP)

(72) Inventors: Kenji Murakami, Ehime (JP); Masato Kagiyama, Ehime (JP); Tooru Aoki, Ehime (JP); Yoshihiro Kataoka, Ehime (JP); Takahiko Tanida, Ehime (JP); Hiroshi Suzuki, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 393 days.

(21) Appl. No.: 14/647,826

(22) PCT Filed: Dec. 13, 2013

(86) PCT No.: PCT/JP2013/007351
§ 371 (c)(1),
(2) Date: May 28, 2015

(87) PCT Pub. No.: WO2014/091765
PCT Pub. Date: Jun. 19, 2014

(65) Prior Publication Data
US 2015/0328404 A1 Nov. 19, 2015

(30) Foreign Application Priority Data
Dec. 13, 2012 (JP) .................................. 2012-271961

(51) Int. Cl.
*A61M 31/00* (2006.01)
*A61M 5/00* (2006.01)
(Continued)

(52) U.S. Cl.
CPC .......... *A61M 5/20* (2013.01); *A61M 5/31583* (2013.01); *A61M 5/347* (2013.01);
(Continued)

(58) Field of Classification Search
CPC .... A61M 2005/206; A61M 2005/2403; A61M 2005/2407; A61M 2005/2496; A61M 2005/3125; A61M 2005/31588; A61M 2205/14; A61M 2205/52; A61M 2205/6072; A61M 2205/6081; A61M 5/20; A61M 5/31583
See application file for complete search history.

(56) References Cited

U.S. PATENT DOCUMENTS 7,704,231 B2 4/2010 Pongpairochana et al.
7,967,784 B2 6/2011 Pongpairochana et al.
(Continued)

FOREIGN PATENT DOCUMENTS

JP H11-513586 A 11/1999
JP 4614621 B2 1/2011
(Continued)

OTHER PUBLICATIONS

The Search Report from the corresponding European Patent Application No. 13862901.9 dated Dec. 3, 2015.
(Continued)

*Primary Examiner* — Rebecca E Eisenberg
(74) *Attorney, Agent, or Firm* — Shinjyu Global IP

(57) ABSTRACT

The pharmaceutical injection device of the present invention comprises a cartridge holder, a main case, a piston, a motor, an opening component, an open/closed detection switch, and a controller. The motor drives the piston in either an insertion direction in which the piston is inserted into a pharmaceutical cartridge, or a pull-out direction in which the piston is pulled out of the pharmaceutical cartridge. The opening component opens the cartridge holder in conjunction with the movement of the piston in the pull-out direction. The open/closed detection switch detects whether the cartridge holder is open or closed. When the open/closed detection switch detects that the cartridge holder is open, the controller controls the motor so as to stop the piston.

16 Claims, 28 Drawing Sheets

(51) Int. Cl.
*A61M 5/20* (2006.01)
*A61M 5/315* (2006.01)
*A61M 5/34* (2006.01)
*A61M 5/24* (2006.01)
*A61M 5/31* (2006.01)

(52) U.S. Cl.
CPC ............ *A61M 2005/206* (2013.01); *A61M 2005/2403* (2013.01); *A61M 2005/2407* (2013.01); *A61M 2005/2496* (2013.01); *A61M 2005/3125* (2013.01); *A61M 2005/31588* (2013.01); *A61M 2202/0007* (2013.01); *A61M 2205/14* (2013.01); *A61M 2205/27* (2013.01); *A61M 2205/276* (2013.01); *A61M 2205/52* (2013.01); *A61M 2205/6072* (2013.01); *A61M 2205/6081* (2013.01)

(56) References Cited

U.S. PATENT DOCUMENTS

| 8,376,985 | B2 | 2/2013 | Pongpairochana et al. |
| 9,492,616 | B2* | 11/2016 | Eggert .................... A61M 5/20 |
| 2003/0161744 | A1 | 8/2003 | Vilks et al. |
| 2007/0197968 | A1 | 8/2007 | Pongpairochana et al. |
| 2010/0160857 | A1 | 6/2010 | Pongpairochana et al. |
| 2011/0201998 | A1 | 8/2011 | Pongpairochana et al. |
| 2012/0071819 | A1 | 3/2012 | Brüggemann et al. |
| 2013/0245604 | A1* | 9/2013 | Kouyoumjian ..... A61M 5/1408 604/506 |

FOREIGN PATENT DOCUMENTS

| JP | 2012-34729 A | 2/2012 |
| JP | 2012-50847 A | 3/2012 |
| JP | 2012-516737 A | 7/2012 |
| JP | 5089991 B2 | 12/2012 |
| WO | 1997/014459 A1 | 4/1997 |
| WO | 2002/051475 A1 | 7/2002 |
| WO | 2005/077441 A2 | 8/2005 |
| WO | 2010089310 A1 | 8/2010 |
| WO | 2012032411 A2 | 3/2012 |
| WO | 2012/160160 A1 | 11/2012 |

OTHER PUBLICATIONS

The Search Report from the corresponding International Patent Application No. PCT/JP2013/007351 dated Mar. 25, 2014.

* cited by examiner

PHARMACEUTICAL INJECTION DEVICE

PRIORITY

This application is a U.S. National stage application of International Application PCT/JP2013/007351, with an international filing date of Dec. 13, 2013, which claims priority to Japanese Patent Application No. 2012-271961 filed on Dec. 13, 2012. The entire disclosures of International Application PCT/JP2013/007351 and Japanese Patent Application No. 2012-271961 are hereby incorporated herein by reference.

TECHNICAL FIELD

Embodiments of the present invention relate to a pharmaceutical injection device for injecting insulin, growth hormone, or another such pharmaceutical, for example.

BACKGROUND

A conventional pharmaceutical injection device of this type comprised a main case, a cartridge holder provided openably and closeably to this main case, a piston that is provided inside this main case so as to be able to protrude from a pharmaceutical cartridge held in the cartridge holder, a piston drive mechanism that can make this piston protrude from the pharmaceutical cartridge, and a controller that is connected to this drive mechanism (see Patent Literature 1 below, for example).

Patent Literature 1: Japanese Laid-Open Patent Application 2012-50847

SUMMARY

The conventional pharmaceutical injection device discussed above is configured so that the piston is inserted into the pharmaceutical cartridge held in the cartridge holder, which injects the pharmaceutical that fills this pharmaceutical cartridge from the injection needle into the body.

When the pharmaceutical cartridge is replaced, an eject button provided to the main case is pressed in a state in which the piston has been pulled out of the pharmaceutical cartridge, which opens the cartridge holder, and the pharmaceutical cartridge is replaced in this state.

That is, replacing the pharmaceutical cartridge requires the operation of an eject button, and the eject button is configured as a slide switch to prevent the cartridge holder from opening up if the eject button should be pressed unintentionally.

Therefore, depending on who injects the pharmaceutical, some people may find it difficult to operate this eject button, making it difficult to open the cartridge holder.

In view of this, and in light of the problems encountered with the conventional pharmaceutical injection device discussed above, it is an object of certain embodiments of the present invention to provide a pharmaceutical injection device with which the cartridge holder can be opened more easily.

In one aspect of the present invention, a pharmaceutical injection device comprises a cartridge holder, a main case, a piston, a driver, an opening component, a cartridge holder detector, and a controller. The pharmaceutical cartridge is mounted to the cartridge holder. The cartridge holder is provided openably and closeably to the main case. The piston can be inserted into the pharmaceutical cartridge mounted to the cartridge holder. The driver drives the piston to move in either an insertion direction in which the piston is inserted into the pharmaceutical cartridge, or a pull-out direction in which the piston is pulled out of the pharmaceutical cartridge. The opening component opens the cartridge holder in conjunction with the movement of the piston in the pull-out direction. The cartridge holder detector detects whether the cartridge holder is open or closed. The controller controls the driver so as to stop the piston when the cartridge holder detector has detected that the cartridge holder is open.

Because the cartridge holder is thus opened in conjunction with movement of the piston in the pull-out direction, the user can easily replace the pharmaceutical cartridge without having to operate an eject button or the like.

Embodiments of the present invention relate to a pharmaceutical injection device with which the cartridge holder can be easily opened.

DETAILED DESCRIPTION

Embodiments of the present invention will now be described in detail through reference to the drawings.

1. Configuration

1-1. External Configuration of Pharmaceutical Injection Device

Figure 1:
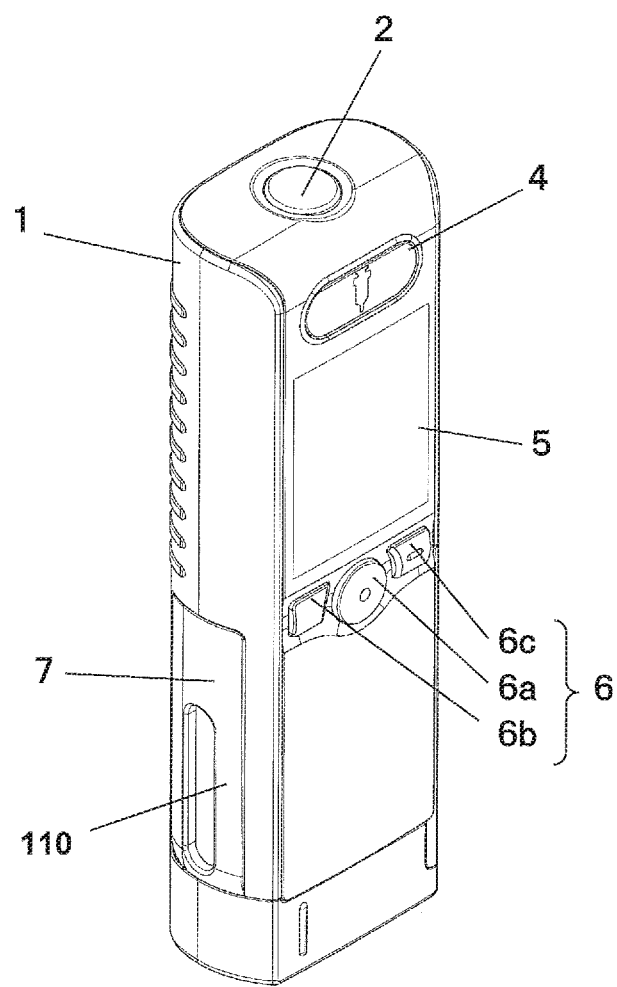
FIG. 1 is an oblique view of the pharmaceutical injection device in Embodiment 1 pertaining to the present invention.
Figure 2:
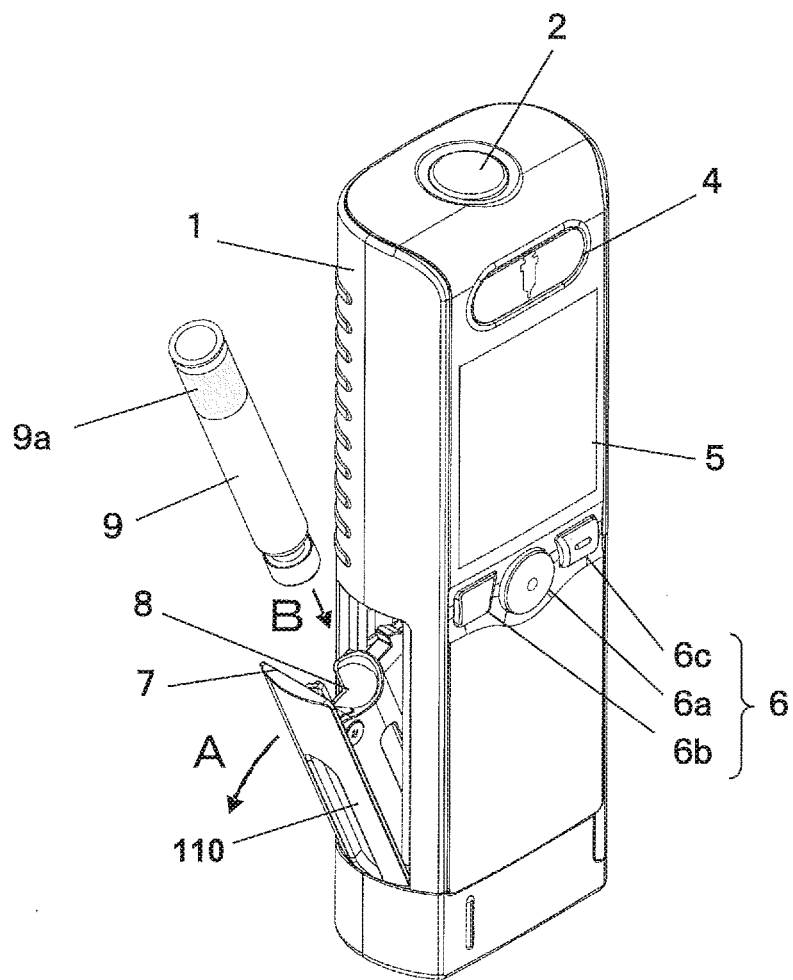
FIG. 2 is an oblique view of the state when the cartridge holder of the pharmaceutical injection device shown in FIG. 1 has been opened.
Figure 3:
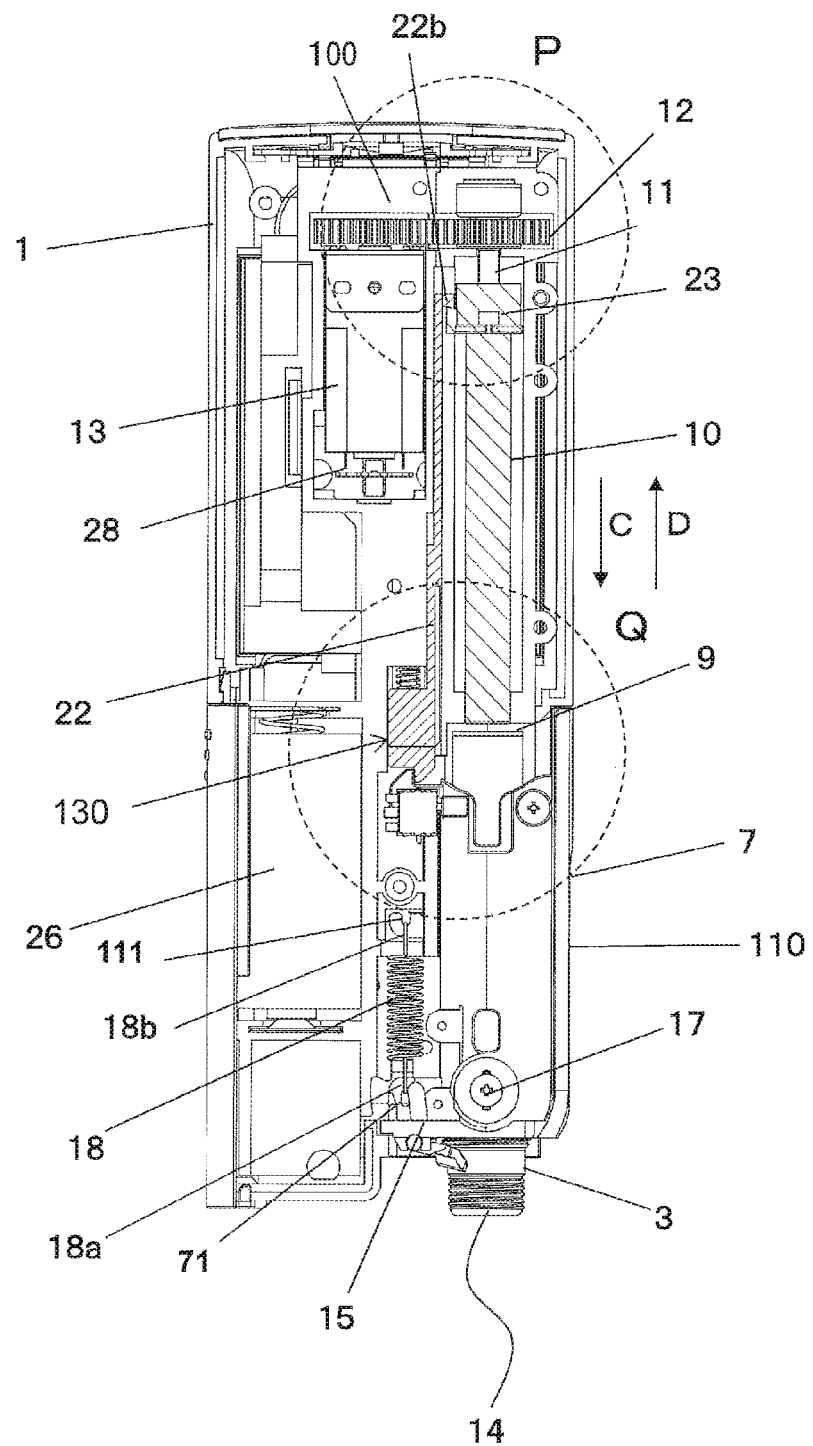
FIG. 3 is a front cross section of the internal configuration of the pharmaceutical injection device shown in FIG. 1.

FIG. 1 is an oblique view of the pharmaceutical injection device in this embodiment. FIG. 2 is an oblique view of the state when the cartridge holder of the pharmaceutical injection device in this embodiment has been opened. FIG. 3 is a front cross section of the internal configuration of the pharmaceutical injection device in this embodiment.

As shown in FIGS. 1 and 2, the pharmaceutical injection device in this embodiment comprises a tubular main case 1. A power switch 2 is provided to the top face of this main case 1, and an injection needle mounting component 3 is provided to the bottom face as shown in FIG. 3. In this Specification, for the sake of convenience, the side on which the power switch 2 is provided is the upper side, and the side on which the injection needle mounting component 3 is provided (the opposite site) is the lower side.

A pharmaceutical injection switch 4, a display component 5, and a setting switch 6 for setting the pharmaceutical dose are provided in that order, from top to bottom, to the surface portion of this main case 1. This setting switch 6 has a middle switch 6a, a left switch 6b disposed to the left (in the drawing) of the middle switch 6a, and a right switch 6c disposed to the right (in the drawing) of the middle switch 6a. An LCD panel or the like can be used as the display component 5. The side on which the display component 5 is provided will be called the front side of the pharmaceutical injection device, and the opposite side the rear side.

As shown in FIGS. 1 and 2, the main case 1 is provided with a cartridge holder 7 for openably and closeably mounting a tubular pharmaceutical cartridge 9.

That is, first the cartridge holder 7 is opened as indicated by the arrow A in FIG. 2, and then the pharmaceutical cartridge 9 is inserted as indicated by the arrow B through an insertion opening 8 provided to the top face of the cartridge holder 7, and when the cartridge holder 7 is then closed as shown in FIG. 1, the pharmaceutical cartridge 9 is mounted inside the main case 1 as shown in FIG. 3. An outer wall 110 is provided to the outside of the cartridge holder 7, and this outer wall 110 forms the outer face of the pharmaceutical injection device when the cartridge holder 7 is closed.

1-2. Internal Configuration of Pharmaceutical Injection Device

As shown in FIGS. 3, 4A, 4B, and 4C, a piston 10 is provided above the insertion opening 8 of the cartridge holder 7 inside the main case 1.

Figure 4A:
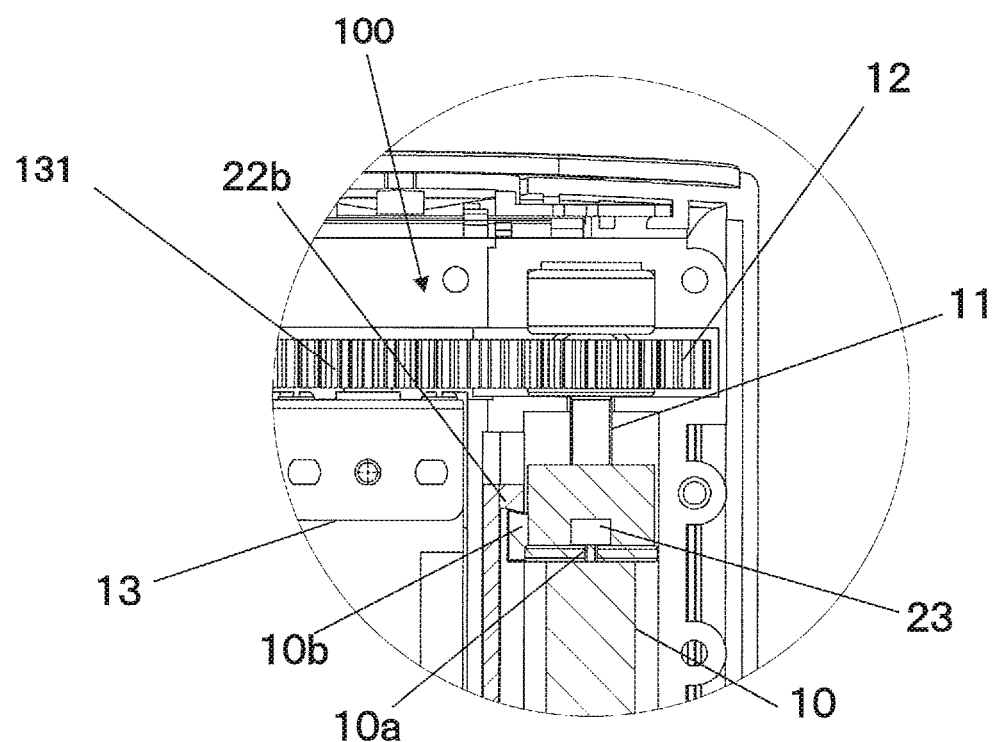
FIG. 4A is a detail view of the main components of the pharmaceutical injection device shown in FIG. 3.
Figure 4B:
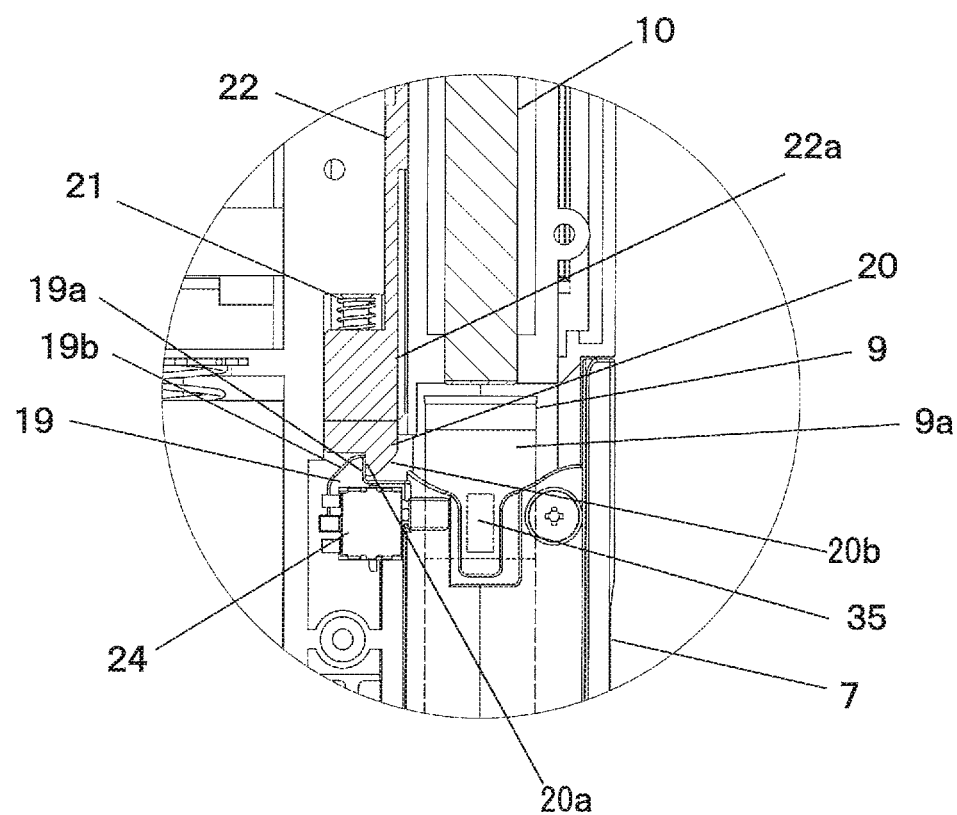
FIG. 4B is a detail view of the main components of the pharmaceutical injection device shown in FIG. 3.
Figure 4C:
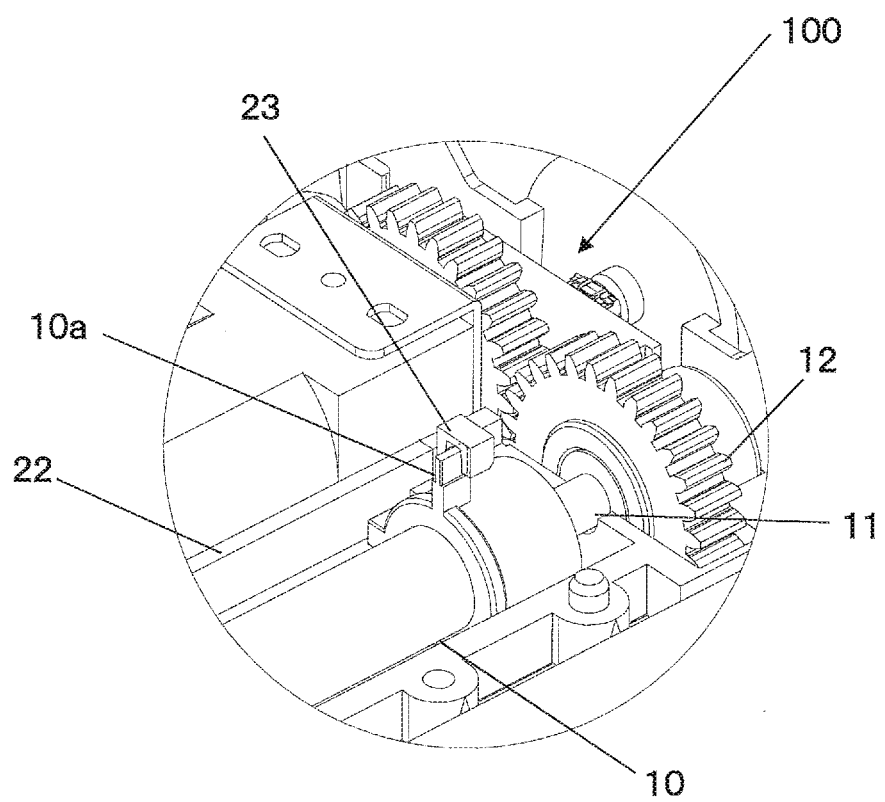
FIG. 4C is an oblique view of the main components of the pharmaceutical injection device shown in FIG. 3.

FIG. 4A is a detail view of the P part in FIG. 3, and shows the configuration near an origin sensor 23 in this embodiment. FIG. 4B is a detail view of the Q part in FIG. 3, and is a cross section of near the insertion opening 8 of the cartridge holder 7. FIG. 4C is an oblique view of the configuration near the origin sensor 23, and shows the state when the piston 10 is disposed at the origin position (an example of a reference position). FIGS. 3, 4A, 4B, and 4C all show the state when the cartridge holder 7 is closed and the piston 10 is disposed at the origin position.

The "origin position" that is an example of the reference position of the piston 10 is a position at which the piston 10 is to the rear (the upper side) of the rear end of the pharmaceutical cartridge 9 mounted to the cartridge holder 7. Specifically, when the cartridge holder 7 is opened and closed, the piston 10 is in a position where the piston 10 does not interfere with the pharmaceutical cartridge 9.

As shown in FIG. 4A, the piston 10 is moved in and out of the pharmaceutical cartridge 9 through the insertion opening 8 in the cartridge holder 7 by a piston drive mechanism 100 composed of a feed screw 11, a gear 12, and a motor 13 (an example of a driver).

To describe this in further detail, the motor 13 is disposed so that its drive shaft is substantially parallel to the piston 10. A drive gear 131 that is linked to the shaft of the motor 13 is provided on the upper side of the motor 13. A threaded hole is formed on the inside of the piston 10, and the feed screw 11 meshes with this threaded hole. The rotation of the feed screw 11 moves the piston 10 up and down in FIG. 3. The feed screw 11 is fixed to the gear 12 disposed above the piston 10, and the gear 12 meshes with the drive gear 131. With this configuration, the rotation of the motor 13 is transmitted through the drive gear 131 and the gear 12 to the feed screw 11, causing the feed screw 11 to rotate and drive the piston 10.

The insertion direction in which the piston 10 is inserted into the pharmaceutical cartridge 9 mounted to the cartridge holder 7 (also referred to as downward or the forward direction) is indicated by the arrow C, and the pull-out direction in which the piston 10 is pulled out of the pharmaceutical cartridge 9 mounted to the cartridge holder 7 (also referred to as upward or the rearward direction) is indicated by the arrow D.

1-3. Configuration of Cartridge Holder 7 and its Surroundings

The pharmaceutical injection device in this embodiment is further provided with an opening component 130 that opens the cartridge holder 7 with respect to the main case 1, an open/closed detector switch 24 that detects whether or not the cartridge holder 7 is closed, a needle detector switch 15 that detects whether or not an injection needle 16 has been mounted to the injection needle mounting component 3, and an identification component 35 that detects whether or not the pharmaceutical cartridge 9 has been mounted to the cartridge holder 7 and reads an identification label 9a affixed to the pharmaceutical cartridge 9. The components of the cartridge holder 7 among above components will now be described in order.

1-3-1. Cartridge Holder 7

The cartridge holder 7 will be described in detail through reference to FIGS. 1 to 4B.

As shown in FIGS. 2 and 3, the cartridge holder 7 is tubular in shape, with the insertion opening 8 in its top face, and an opening 14 is also provided to the bottom face. The outer peripheral part of this opening 14 is threaded, and this becomes the injection needle mounting component 3, to which the injection needle is mounted.

An axial support component 17 that axially supports the cartridge holder 7 so that it can open and close with respect to the main case 1 is provided to the lower outer peripheral face of the cartridge holder 7, that is, on the opening 14 side of the cartridge holder 7.

Also, one end of an ejector spring 18 (an example of a biasing member) is linked to a part of the cartridge holder 7 at the opposite side (the inside) of the axial support component 17 from the direction in which the cartridge holder 7 opens. This ejector spring 18 is part of the opening component 130. The other end of the ejector spring 18 is linked to the main case 1 above.

Specifically, a holder-side linking component 71 that links to the first end 18a of the ejector spring 18 is formed on the inside portion of the end on the opening 14 side of the cartridge holder 7. Also, the ejector spring 18 is disposed along the cartridge holder 7 on the inside of the cartridge holder 7 in a closed state, and the second end 18b of the ejector spring 18 is linked to a main body-side linking component 111 formed on the main case 1 on the insertion opening 8 side.

That is, the cartridge holder 7 is subjected to a force in the direction in which the ejector spring 18 contracts, and the insertion opening 8 portion that is a upper portion of the cartridge holder 7 is biased in the opening direction with respect to the main case 1 as shown in FIG. 2.

Also, a latched component 19 is provided as shown in FIG. 4B to the upper part of the cartridge holder 7 in order to hold the cartridge holder 7 in its closed position as shown in FIGS. 1 and 3 against the biasing in the opening direction by the ejector spring 18.

1-3-2. Configuration of Opening Component 130

The opening component 130 has the above-mentioned ejector spring 18, an ejector finger 20, a lever 22, and protrusions 22a and 22b.

As shown in FIG. 4B, the ejector finger 20 is provided above the latched component 19 in the main case 1. As shown in FIG. 3, the ejector finger 20 is linked adjacent to the protrusion 22a on the lower end side of the slender lever 22. A spring 21 is in contact with the opposite side of the protrusion 22a from the ejector finger 20, and the protrusion 22a and the ejector finger 20 are biased toward the latched component 19 below (the insertion direction C) (see FIGS. 3 and 4B).

Also, the ejector finger 20 has on its inside a contact face 20a formed parallel to the movement direction of the piston 10. The latched component 19 has on its outside a contact face 19a formed parallel to the movement direction of the piston 10, in a state in which the cartridge holder 7 is closed. When the contact face 20a and the contact face 19a come into contact with each other, this keeps the cartridge holder 7 closed.

The ejector finger 20 also has an inclined part 20b that is inclined outward from the lower end of the contact face 20a. The latched component 19 has an inclined part 19b that is inclined inward from the upper end of the contact face 19a. As discussed below, when the user closes the cartridge holder 7, the inclined part 20b slides with respect to the inclined part 19b, allowing smooth closure.

The lever 22 has at its upper end a protrusion 22b disposed diagonally across from the protrusion 22a (at a position where the protrusion direction is reversed), and the protrusion 22b is provided on the feed screw 11 side of the piston 10.

Specifically, as shown in FIG. 3, the slender lever 22 is disposed along the movement direction of the piston 10, along the inside of the piston 10 when it has not yet been inserted into the pharmaceutical cartridge 9. The protrusion 22a and the ejector finger 20 are provided on the cartridge holder 7 side of the lever 22, and the protrusion 22b is provided on the gear 12 side of the lever 22. Thus, the lever 22 links the protrusion 22b and the ejector finger 20, and the lever 22, the protrusion 22b, and the ejector finger 20 are biased downward by the spring 21 so as to latch the latched component 19.

1-3-3. Origin Sensor 23

As shown in FIGS. 4A and 4C, the origin sensor 23, which senses the origin position of the piston 10, is provided on the rear end side of the piston 10 (the upper end side (the pull-out direction D side) in FIG. 1). This origin sensor 23 is fixed on the inside of the main case 1.

The origin sensor 23 can be a transmission type of photoelectric sensor, for example. When the edge on the rear end side of a protrusion 10a provided to the piston 10 (the edge on the pull-out direction D side) crosses the origin sensor 23, a detection signal is sent to a controller 25 (discussed below), and the piston position at this point (the piston position shown in FIG. 4C) is termed the origin position (an example of a reference position) of the piston 10.

A protrusion 10b that protrudes to the lever 22 side is provided to the piston 10. This protrusion 10b is formed at a position where it hits the protrusion 22b of the lever 22 only when the piston 10 retracts upward from the origin position (moves in the pull-out direction D), on the insertion direction C side of the protrusion 22b. When the protrusion 10b hits the protrusion 22b and retracts the protrusion 22b, the entire lever 22 is retracted along with the protrusion 22b (moved upward in FIGS. 1 and 2).

Figure 5:
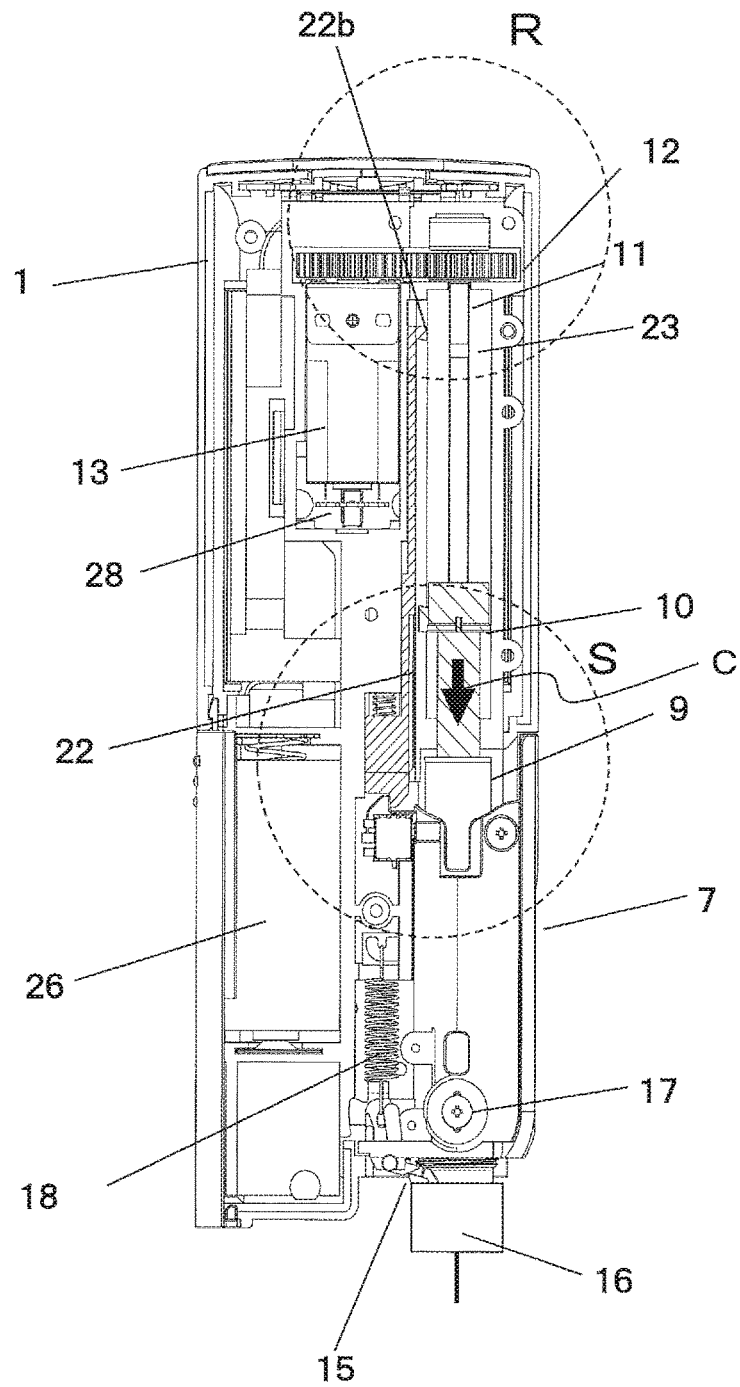
FIG. 5 is a front cross section of the internal configuration of the pharmaceutical injection device shown in FIG. 1.
Figure 6A:
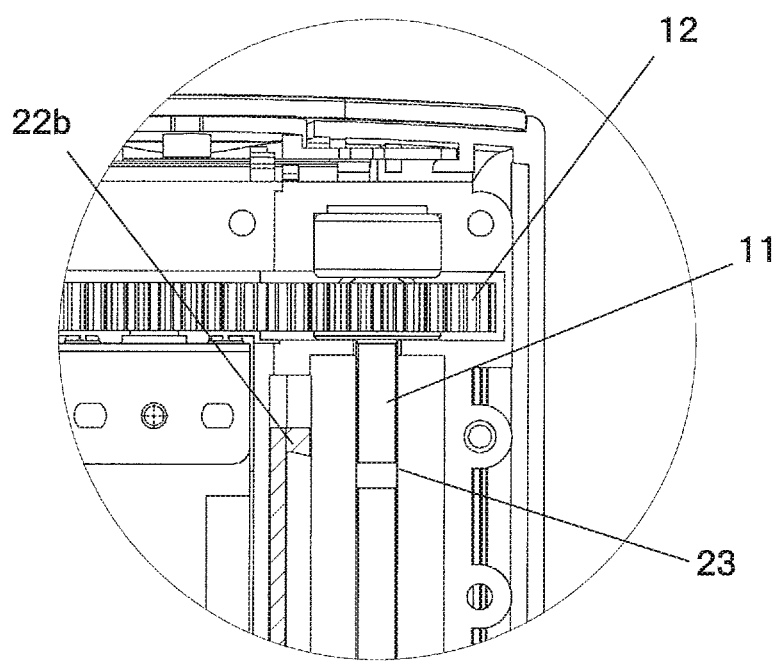
FIG. 6A is a detail view of the main components of the pharmaceutical injection device shown in FIG. 5.
Figure 6B:
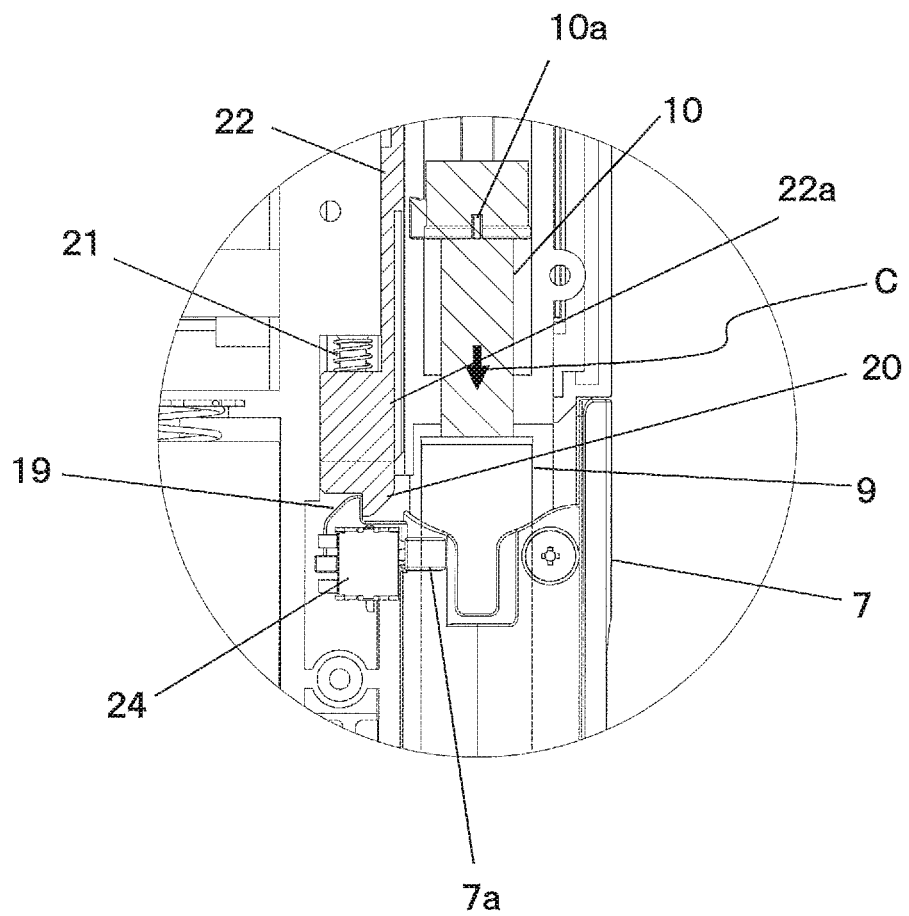
FIG. 6B is a detail view of the main components of the pharmaceutical injection device shown in FIG. 5.
Figure 6C:
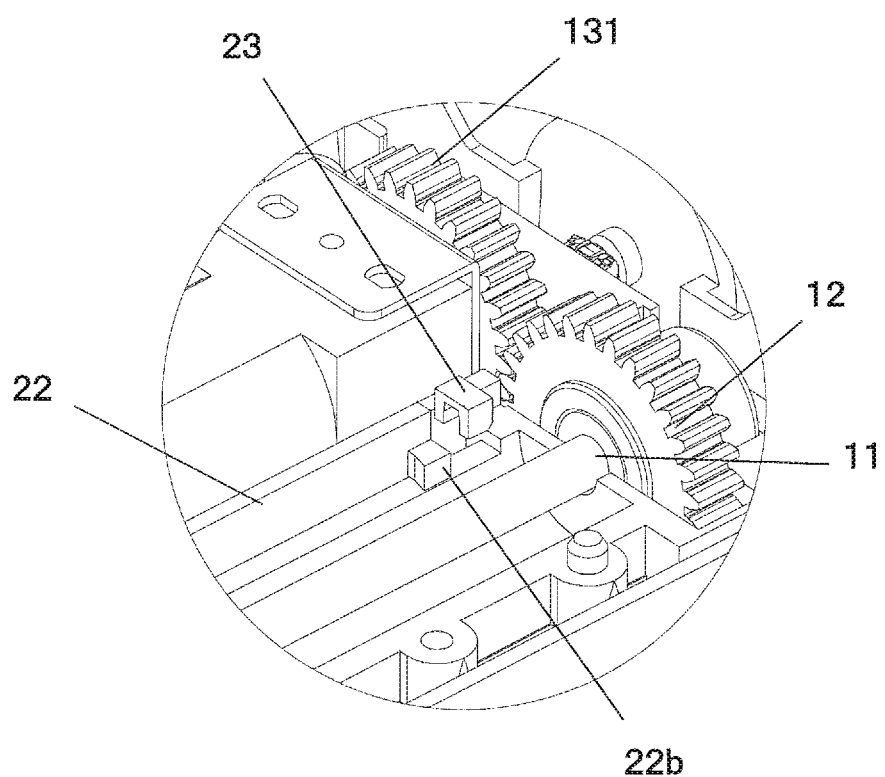
FIG. 6C is an oblique view of the main components of the pharmaceutical injection device shown in FIG. 5.

FIG. 5 shows the internal configuration of the pharmaceutical injection device in this embodiment. FIG. 6A shows the configuration near the origin sensor 23 in this embodiment. FIG. 6B is a cross section of near the insertion opening 8 of the cartridge holder 7, and is a detail view of the S part of FIG. 5. FIG. 6C is an oblique view of the configuration near the origin sensor 23. FIGS. 5, 6A, 6B, and 6C all show the state when the piston 10 is moved in the insertion direction C in order to inject a pharmaceutical.

Meanwhile, during pharmaceutical injection (the state in FIGS. 5 and 6A to 6C), when the piston 10 moves downward (in the insertion direction C; that is, when it moves downward from the origin position), the protrusion 22b of the lever 22 moves downward along with the protrusion 10b of the piston 10, but the lever 22 stays at the position shown in FIG. 3 (the lower end position), and does not descend any further, so the protrusion 22b on the upper end side of the lever 22 moves away from the protrusion 10b of the piston 10. This structure in which there is no descent can be achieved, for example, by configuring the lever 22, the protrusion 22b, and the ejector finger 20 to hit a protrusion (not shown) and stop upon reaching the position shown in FIG. 3. The position from which the ejector finger 20 does not descend is a dotted line position shown in FIG. 13B (discussed below).

Thus, with this structure, the latched component 19 provided inside the main case 1 engages with the ejector finger 20 that is adjacent to the protrusion 22a on the lower end side of the lever 22, which keeps the cartridge holder 7 closed.

The engagement between the latched component 19 inside the main case 1 and the ejector finger 20 attached to the protrusion 22a on the lower end side of the lever 22 is only released and the cartridge holder 7 opened when the piston 10 returns to its origin position after all of the pharmaceutical in the pharmaceutical cartridge has been injected, and the piston 10 then moves upward.

In the above example, the ejector finger 20 and the lever 22 are separate members that are linked together, but this is not the only option, and they may be formed integrally instead.

1-3-4. Open/Closed Detector Switch 24

The pharmaceutical injection device in this embodiment is provided with a open/closed detector switch 24 that detects that the cartridge holder 7 has been closed. The open/closed detector switch 24 is a push-type detector switch, for example, and as shown in FIGS. 3 and 4B, it is disposed near the upper end of the cartridge holder 7. When the cartridge holder 7 is closed, the side face 7a of the cartridge holder 7 pushes the open/closed detector switch 24 to its on state, and it is detected that the cartridge holder 7 has been closed.

1-3-5. Needle Detector Switch 15

The injection needle mounting component 3 is provided with the needle detector switch 15, and as shown in FIG. 5, this needle detector switch 15 detects whether or not the injection needle 16 has been mounted to the injection needle mounting component 3.

FIG. 7a shows the configuration near the injection needle mounting component 3 in a state in which the injection needle 16 has not been mounted. As shown in FIG. 7a, the needle detector switch 15 is disposed near the injection needle mounting component 3. The needle detector switch 15 has a rotary part 150 and a detecting part 151. The rotary part 150 is able to rotate around a rotary shaft 150a, and is biased downward by a spring member or the like (not shown). The detecting part 151 is switched on by upward rotation of the rotary part 150 (see the arrow E), and thereby detects the mounting of the injection needle 16 to the injection needle mounting component 3.

FIG. 7b shows the configuration of the injection needle 16. As shown in FIG. 7b, the injection needle 16 has a cap 160 for mounting to the injection needle mounting component 3. This cap 160 is cylindrical in shape, and is threaded on its inside. The outside of the injection needle mounting component 3 is also threaded, and the injection needle 16 is mounted to the injection needle mounting component 3 by meshing these threads with the threads of the cap 160.

FIG. 7c shows the configuration near the injection needle mounting component 3 in a state in which the injection needle 16 has been mounted. As shown in FIGS. 7a to 7c, when the injection needle 16 is mounted, the rotary part 150 is pushed up by the cap 160 and rotates upward around the rotary shaft 150a. This rotation switches on the detecting part 151, and it is thereby detected that the injection needle 16 has been mounted.

1-3-6. Identification Component 35

As shown in FIG. 4B, the identification component 35 is provided to the main case 1 of the pharmaceutical injection device in this embodiment. This identification component 35 detects whether or not the pharmaceutical cartridge 9 has been mounted to the cartridge holder 7, and also reads the identification label 9a (see FIG. 2) affixed to the pharmaceutical cartridge 9. The identification component 35 is provided at a position opposite the identification label 9a of the pharmaceutical cartridge 9 mounted to the cartridge holder 7.

The identification label 9a is a label (colored marker) applied to the pharmaceutical cartridge 9, and is used to identify the pharmaceutical contained in the pharmaceutical cartridge 9. When the open/closed detector switch 24 detects that the cartridge holder 7 has been closed after the pharmaceutical cartridge 9 has been mounted to the cartridge holder 7, the identification component 35 first detects whether or not there is a pharmaceutical cartridge 9. If the presence of a pharmaceutical cartridge 9 is detected, the identification label 9a affixed to that pharmaceutical cartridge 9 is read, and it is detected whether or not the correct pharmaceutical cartridge 9 has been mounted.

The identification component 35 is configured to include a color sensor, a photosensor, or the like for detecting the presence of a pharmaceutical cartridge 9 and reading the identification label 9a. The color sensor may be a monochrome (such as red or blue) color sensor, or an RGB color sensor for sensing a plurality of colors.

The identification component 35 outputs the detection result for the pharmaceutical cartridge 9 and information read from the identification label 9a to the controller 25.

In the above example, a label written in colored marker is given as an example of the identification label 9a, but this is not the only option, and a color may be applied directly to the pharmaceutical cartridge 9, for instance.

Also, the identification label 9a may be a barcode (one- or two-dimensional). In this case, the identification component 35 is constituted by a BCR (a one- or two-dimensional barcode reader).

1-4. Control Block Configuration of Pharmaceutical Injection Device

Figure 8:
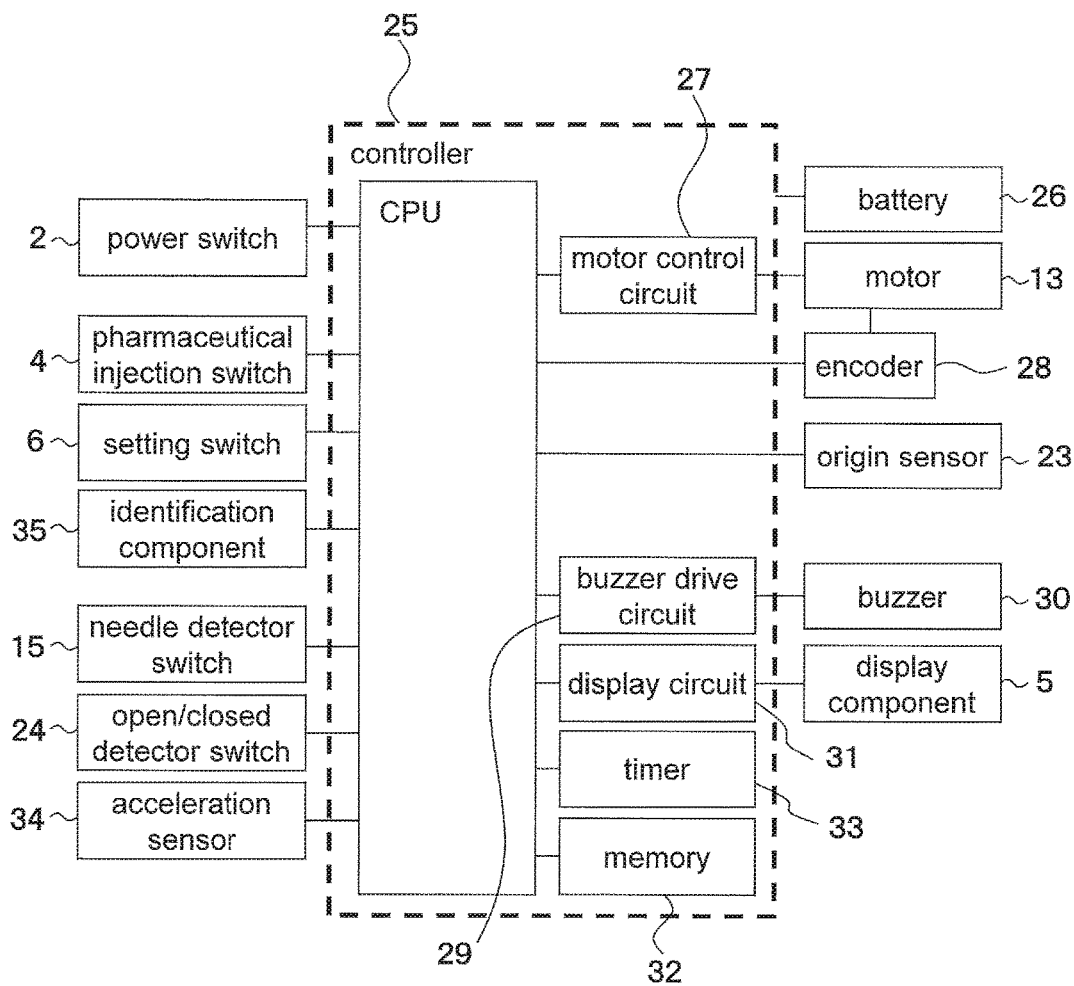
FIG. 8 is a block diagram of the control configuration of the pharmaceutical injection device in FIG. 1.

FIG. 8 is a block diagram of the electrical circuitry in the main case 1 of the pharmaceutical injection device of certain embodiments of the present invention, as well as its surroundings. The controller 25 has a CPU 250, is connected to various I/O interfaces or drive systems, and performs control over these.

More specifically, the CPU 250 of the controller 25 is connected to the power switch 2, the pharmaceutical injection switch 4, the setting switch 6, and other such input components, and checks the input of various control switches.

As a state detection, the needle detector switch 15 that detects whether an injection needle has been mounted, the open/closed detector switch 24 that detects whether the cartridge holder 7 is open or closed, an acceleration sensor 34, and the identification component 35 are connected to the CPU 250 of the controller 25.

In the drive system for the piston 10, the motor 13 that drives the piston 10 is connected to the CPU 250 via a motor control circuit 27 inside the controller 25. Also, for detection of the drive system, an encoder 28 that senses information about the position of the piston 10 is connected to the motor 13, and pulses corresponding to the rotation of the motor 13 are outputted to the CPU 250. The CPU 250 counts the pulses outputted by the encoder 28 to calculate the amount of movement of the piston 10. The CPU 250 is also connected to the origin sensor 23 that senses the origin position of the piston 10, and the CPU 250 uses the output of the encoder 28 and the output of the origin sensor 23 to recognize the current piston position. The CPU 250 is connected to a memory 32, and the recognized current piston position is stored as piston position information. The piston position information is a positive or negative numerical value, and when the piston position information is zero, it means that the piston is in the origin position. When the piston position information is positive, it means that the piston is below the origin position. Conversely, when the piston position information is negative, it means that the piston is above the origin position. The absolute value of the piston position information refers to the movement distance from the origin position.

More specifically, the CPU 250 resets the piston position information stored in the memory 32 to zero (meaning that the piston is in the origin position) when the rear end side of the protrusion 10a provided to the piston 10 has crossed the origin sensor 23. The CPU 250 updates the value every time the encoder 28 connected to the motor 13 outputs a pulse, by adding or subtracting one to or from the piston position information according to the drive direction of the motor 13. In this way, the CPU 250 uses the piston position information stored in the memory 32 to recognize the current piston position. The memory 32 here is constituted by an EEPROM or another such nonvolatile memory, and the piston position information stored in the memory 32 is maintained even when the power to the device is shut off. This piston position information is reset to zero every time the rear end side of the protrusion 10a provided to the piston 10 crosses the origin sensor 23. That is, the origin sensor 23 is used to correct the piston position. The CPU 250 monitors the output of the origin sensor 23, and if the error with respect to zero in the piston position information stored in the memory 32 when the origin sensor 23 senses the origin position exceeds a specific threshold, there is the possibility that some kind of error will occur in the operation of the device, so processing is performed to display a warning on the display component 5 and stop the operation, for example.

In addition, a buzzer 30 that notifies the user when an error has occurred is connected within the controller 25 to the CPU 250 via a buzzer drive circuit 29 that controls the buzzer 30. The display component 5, which displays various messages, numerical values, and so forth, is connected within the controller 25 to the CPU 250 via a dedicated display circuit 31 that controls the display component 5. Furthermore, the memory 32, which stores dose amounts, administration data, and so forth, and a timer 33, which measures elapsed time, are installed in the controller 25 and connected to the CPU 250. A battery is also installed as the power supply for the device, and is connected to the controller 25.

2. Operation

Figure 9:
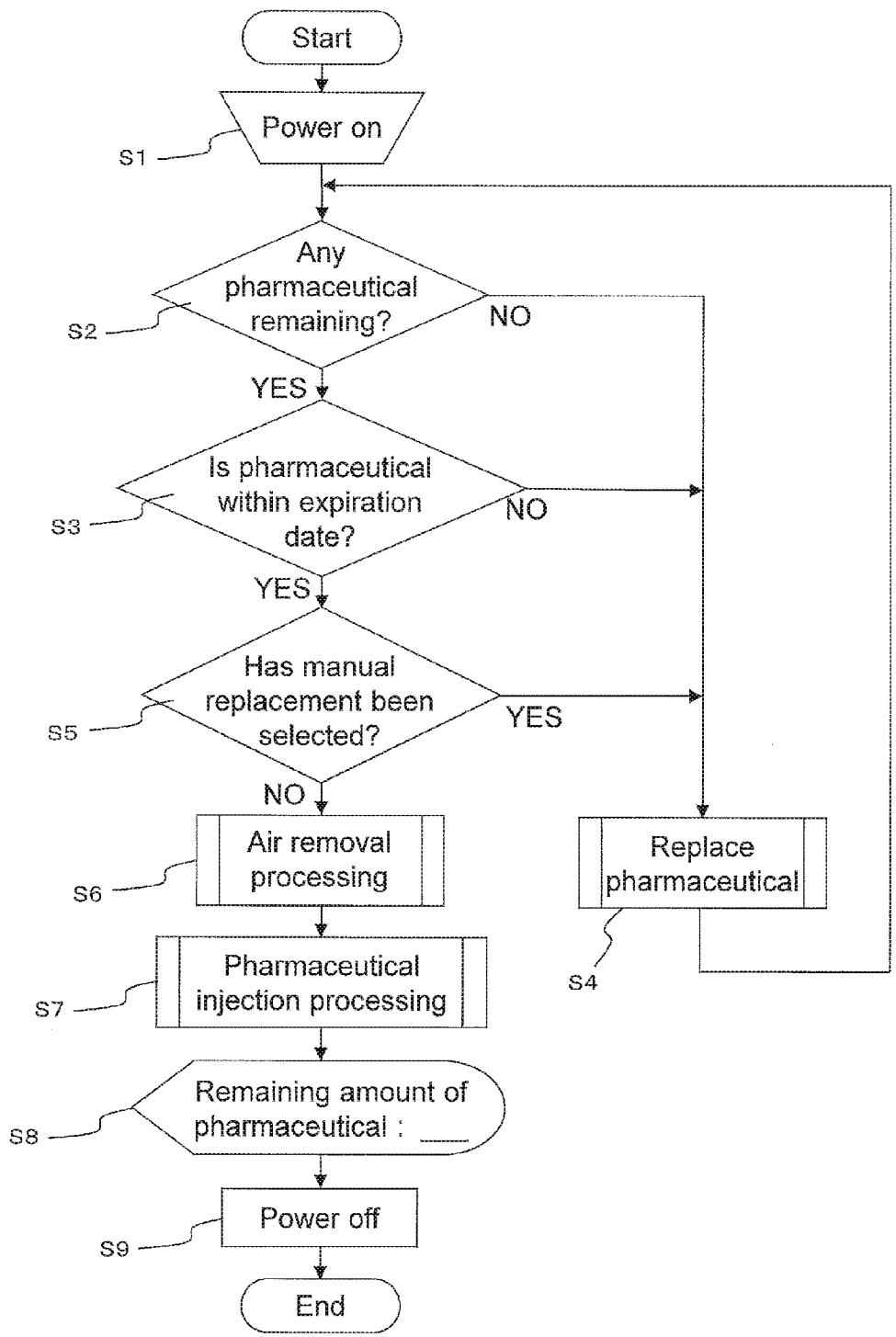
FIG. 9 is a flowchart showing an overview of the operation of the pharmaceutical injection device in FIG. 1.

Next, the operation of the pharmaceutical injection device in this embodiment will be described. FIG. 9 is a flowchart showing an overview of the operation of the pharmaceutical injection device in this embodiment.

2-1. Summary of Overall Operation

First, when the power switch 2 is operated (S1), the controller 25 checks the remaining amount of pharmaceutical (S2), and confirms whether or not the pharmaceutical is within its expiration date (S3). More precisely, the controller 25 records the date and time the pharmaceutical cartridge was last replaced, the number of pharmaceutical injections, the pharmaceutical injection amount, and so forth in the memory 32, and makes a determination on the basis of what is recorded. If there is not enough pharmaceutical, or if the pharmaceutical has passed its expiration date, the control proceeds to S4, and processing is performed for the replacement of the pharmaceutical cartridge 9. At this point a message prompting the user to replace the pharmaceutical may be displayed on the display component 5.

Even if there is still enough pharmaceutical left in the pharmaceutical cartridge 9 and the pharmaceutical is within its expiration date in S2 and S3, if manual replacement of the pharmaceutical has been selected from the menu display in S5, replacement of the pharmaceutical cartridge 9 is carried out by the user.

Air removal processing is the performed (S6).

Once the air removal processing is finished, pharmaceutical injection process (S7) is performed, and the remaining amount of pharmaceutical is displayed (S8).

The power is then switched off, and the operation of the pharmaceutical injection device is ended (S9)

2-2. Air Removal Processing

Next, the air removal processing (S6) shown in FIG. 9 will be described in detail.

Figure 10:
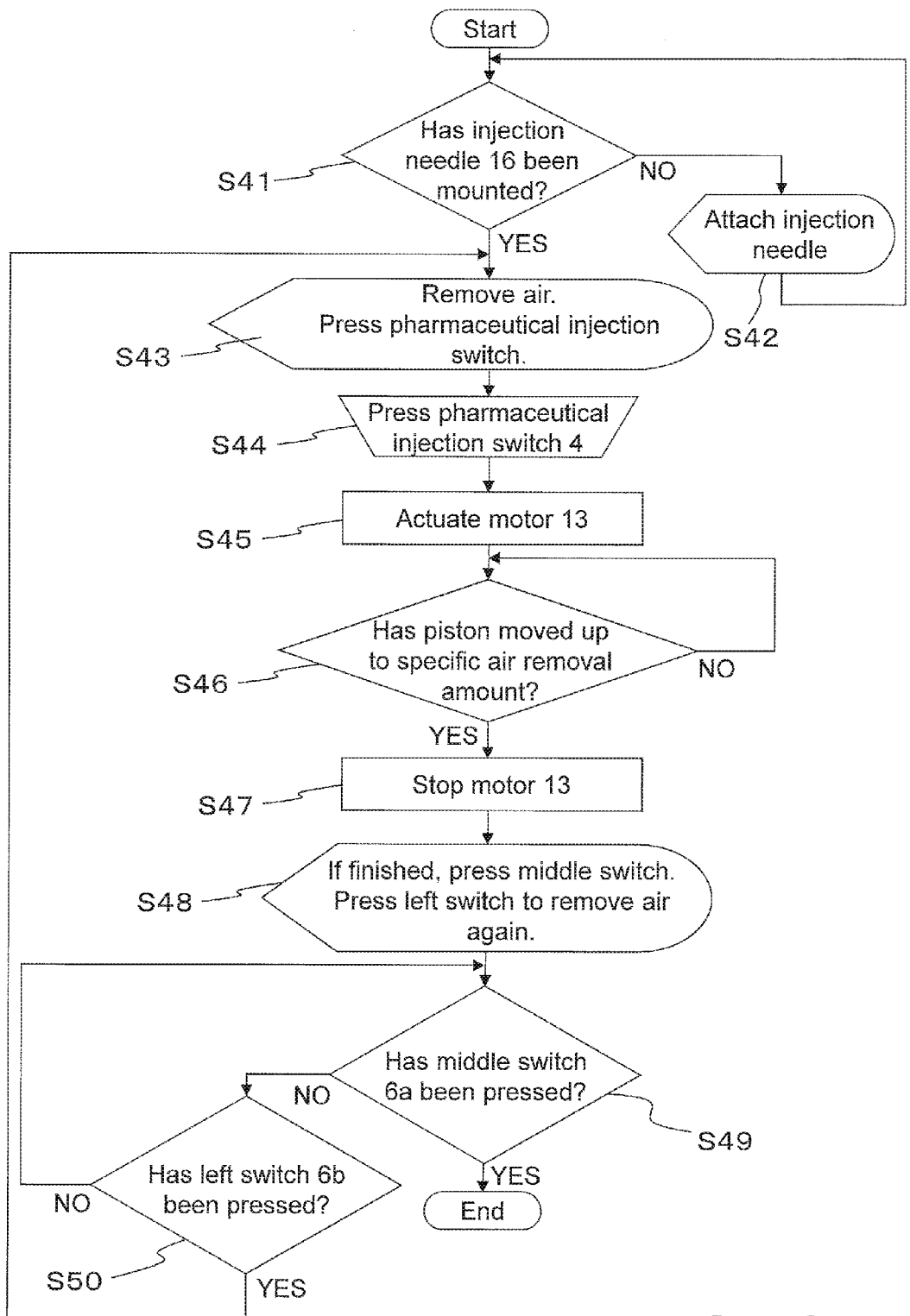
FIG. 10 is a flowchart of air removal processing in the pharmaceutical injection device in FIG. 1.

FIG. 10 is a flowchart of the operation involved in this air removal processing.

First, the controller 25 uses the needle detector switch 15 to check whether or not the injection needle 16 has been mounted to the injection needle mounting component 3 (S41). If it is detected that the injection needle 16 has not been mounted, the controller 25 displays "Attach injection needle" on the display component 5 (S42).

If the injection needle 16 has been mounted, the controller 25 displays "Remove air. Press pharmaceutical injection switch" on the display component 5 (S43).

The user is prompted by the display in S43 to press the pharmaceutical injection switch (S44).

When the pharmaceutical injection switch 4 is pressed, the controller 25 drives the motor 13, the gear 12 meshed with the drive gear 131 of the motor 13 rotates, and this rotation of the gear 12 rotates the feed screw 11, and the rotation is converted into linear motion of the piston 10 (S45).

Next, the controller 25 senses the amount of movement of the piston from the output of the encoder 28, and moves the piston forward by a distance equivalent to a specific amount of air removal (S46).

Once the piston 10 has advanced by a specific amount, the controller 25 then stops the motor 13 and ends the air removal operation (S47).

Next, the controller 25 displays "If finished, press middle switch. Press left switch to remove air again" on the display component 5 (S48). The user at this point visually confirms the air removal state, and selects whether to end the air removal operation or to perform the air removal operation again.

When the middle switch 6a is pressed, the air removal processing is ended (S49). On the other hand, if the left switch 6*b* is pressed (S50), control returns to S43 and the air removal operation is performed again.

In the air removal processing discussed above, the actuation of the air removal operation is also handled by the pharmaceutical injection switch 4, but if an air removal switch (not shown) is provided separately, this air removal switch is used instead. That is, in S44, the motor 13 may be started (S45) by pressing the air removal switch.

2-3. Pharmaceutical Injection Processing

Next, the pharmaceutical injection processing (S7) shown in FIG. 9 will be described in detail.

Figure 11:
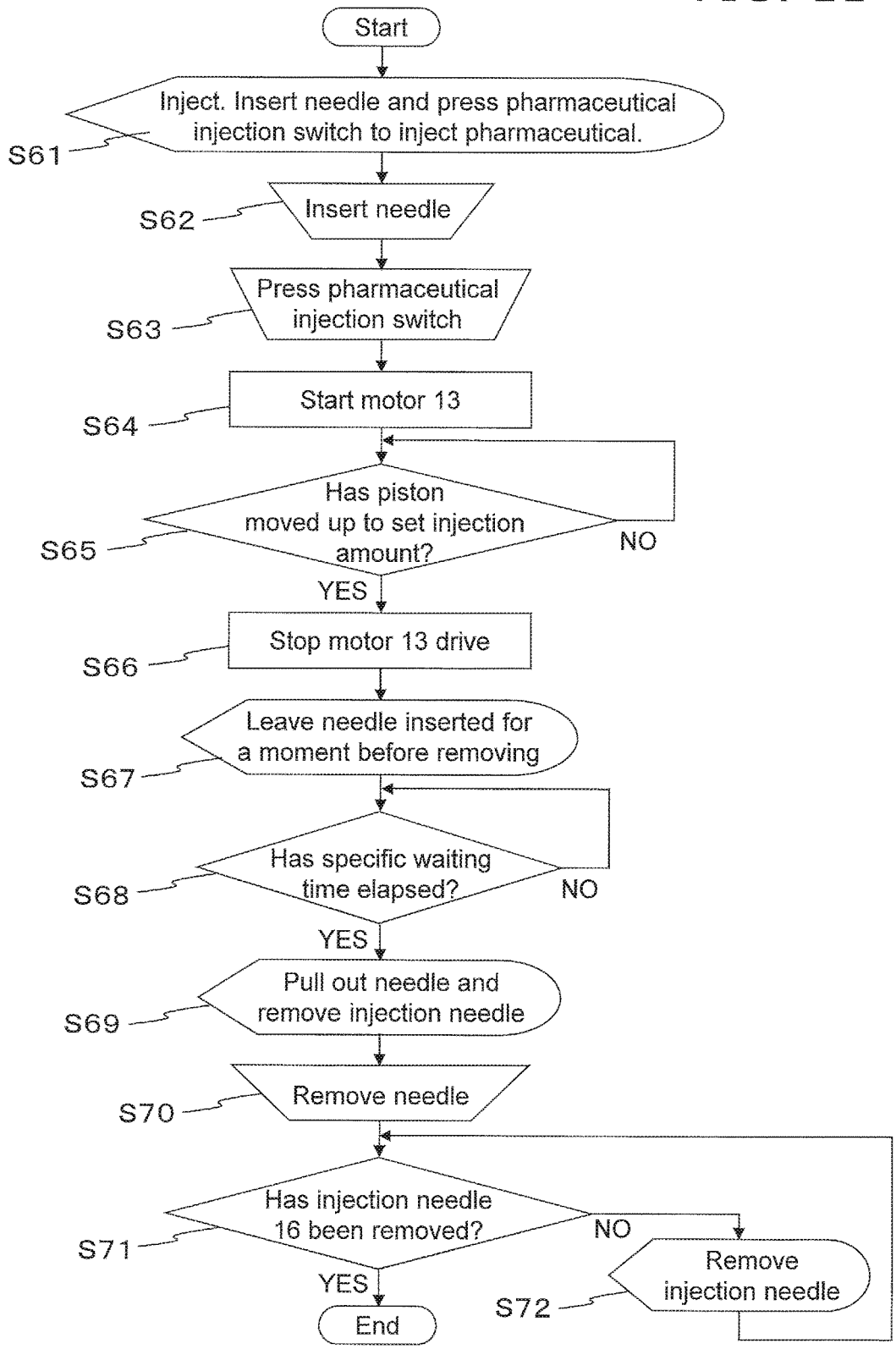
FIG. 11 is a flowchart of pharmaceutical injection processing in the pharmaceutical injection device in FIG. 1.

FIG. 11 is a flowchart of the operation in pharmaceutical injection processing. This pharmaceutical injection processing will be described through reference to FIGS. 5, 6A, 6B, and 6C. The above-mentioned FIGS. 3, 4A, 4B, and 4C show the initial state of the pharmaceutical injection device of certain embodiments of the present invention, but FIGS. 5, 6A, 6B, and 6C show the operation of injecting the pharmaceutical (at the start of the injection operation). The state shown in FIGS. 5, 6A, 6B, and 6C is also the same at the start of the air removal operation discussed above.

First, the controller 25 displays "Inject. Insert needle and press pharmaceutical injection switch to inject pharmaceutical" on the display component 5 (S61). This prompts the user to insert the needle and press the pharmaceutical injection switch 4. The injection of the pharmaceutical contained in the pharmaceutical cartridge is commenced by pressing the pharmaceutical injection switch 4 (see FIG. 2) provided to the outer peripheral surface of the main case 1.

When the user inserts the injection needle into his skin (S62) and presses the pharmaceutical injection switch 4 (S63), the controller 25 starts the motor 13 (S64).

More specifically, this starts the motor 13 (which constitutes the piston drive mechanism 100), the gear 12 linked to the motor 13 rotates, and this rotation of the gear 12 rotates the feed screw 11, and the rotation is converted into linear motion of the piston 10 (see the arrow C in FIG. 5).

When the piston 10 moves downward, the distal end of the piston 10 hits a gasket (not shown) at the rear end of the pharmaceutical cartridge (see FIGS. 6A to 6C), and then the piston 10 is then moved further, the pharmaceutical in the pharmaceutical cartridge 9 is injected through the injection needle 16 mounted to the distal end of the pharmaceutical cartridge 9, and under the skin.

The controller 25 senses the amount of movement of the piston from the output of the encoder 28, and moves the piston 10 in the insertion direction C by a distance equivalent to a specific amount of pharmaceutical injection (S65).

Then controller 25 then stops the motor 13 after the piston 10 has advanced by a specific amount (S66).

The controller 25 then displays "Leave needle inserted for a moment before removing" on the display component 5 so that the user will keep the needle in its inserted state, without removing it, until all of the pharmaceutical has completely stopped coming out of the needle, even after the drive motor 15 has stopped (S67).

After waiting (S68) for a specific length of time (such as 10 seconds) to elapse after the start of the display in S67, the controller 25 causes the display component 5 to display "Pull out needle" (S69). This prompts the user to remove the injection needle 16.

The user removes the injection needle 16 in response to the display on the display component 5 (S70).

When the needle detector switch 15 detects that the injection needle 16 has been removed, the controller 25 ends the pharmaceutical injection processing (S71). If the injection needle 16 has not been removed, the controller 25 causes the display component 5 to display "Remove injection needle" (S72).

2-4. Pharmaceutical Replacement Processing

Next, the pharmaceutical replacement processing (S4) shown in FIG. 9 will be described in detail.

First, the operation when the cartridge holder 7 is ejected (opened) will be described through reference to FIGS. 12, 13A, 13B, and 13C, and after the operation of returning the piston 10 to the origin position has been described through reference to FIGS. 14, 15A, 15B, and 15C, the pharmaceutical replacement processing will be described through reference to a flowchart.

Figure 12:
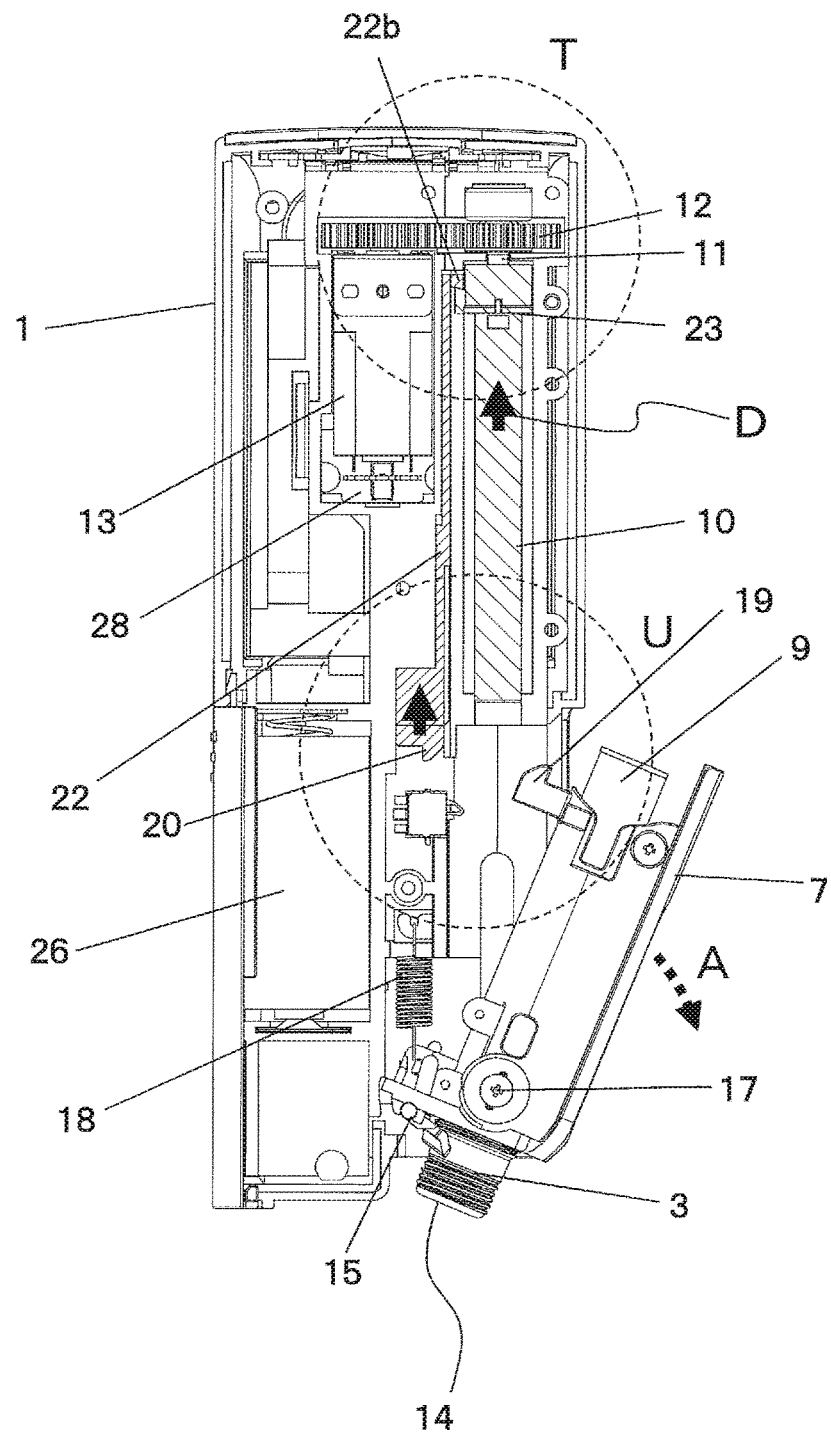
FIG. 12 is a front cross section of the internal configuration of the pharmaceutical injection device shown in FIG. 1.
Figure 13A:
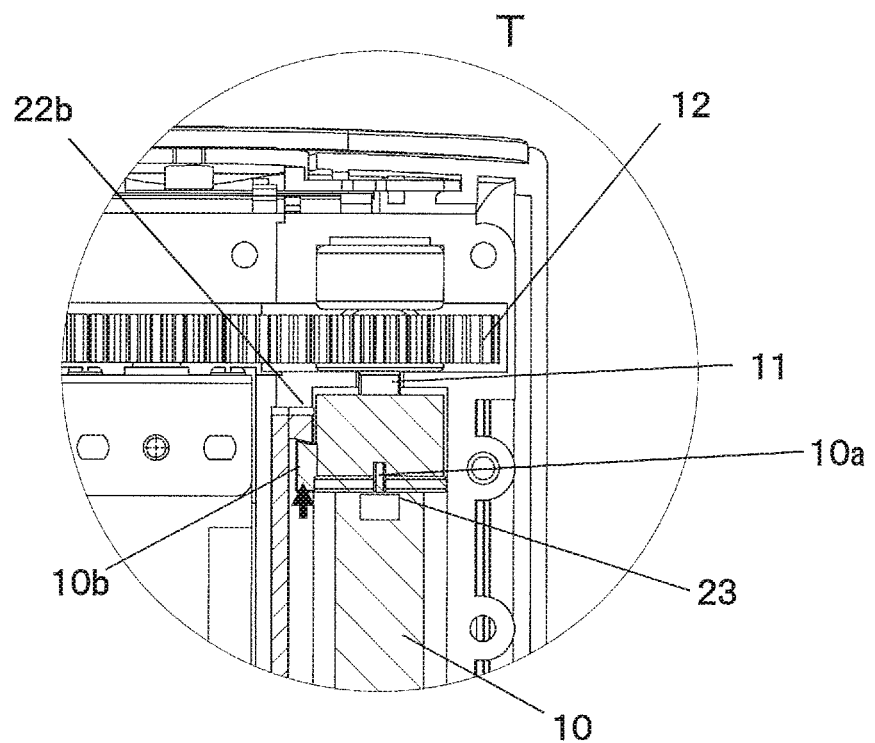
FIG. 13A is a detail view of the main components of the pharmaceutical injection device shown in FIG. 12.
Figure 13B:
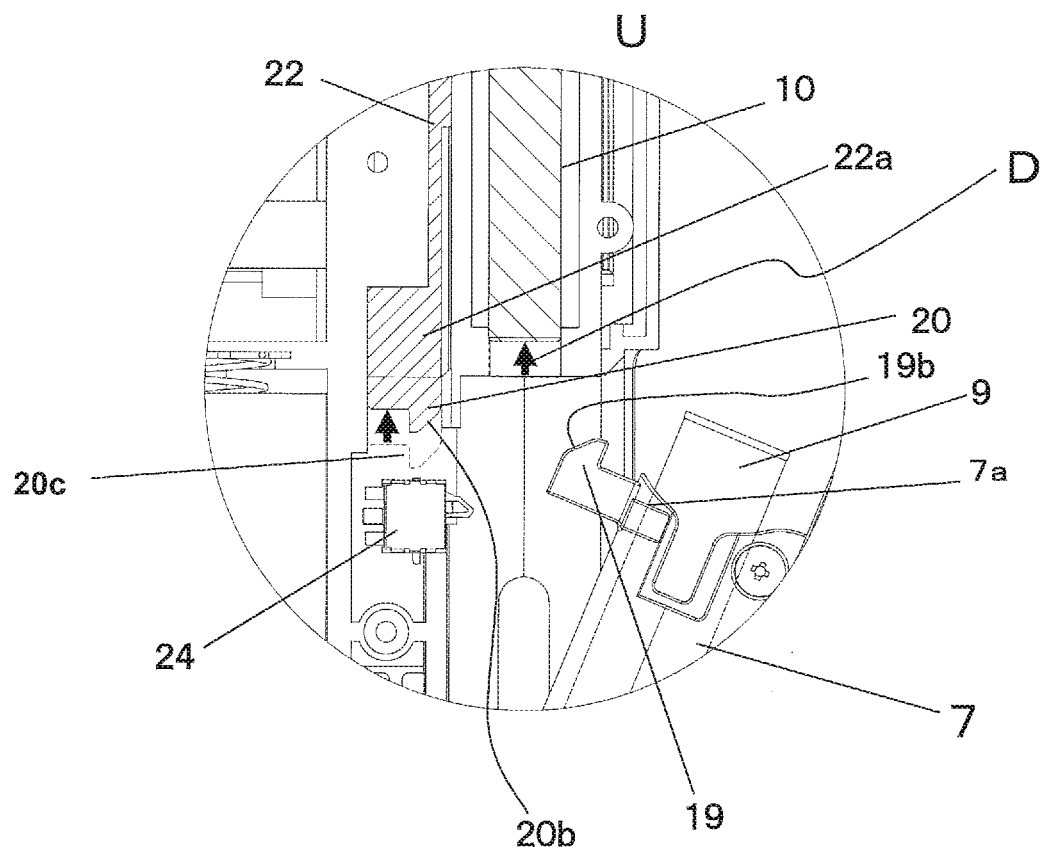
FIG. 13B is a detail view of the main components of the pharmaceutical injection device shown in FIG. 12.
Figure 13C:
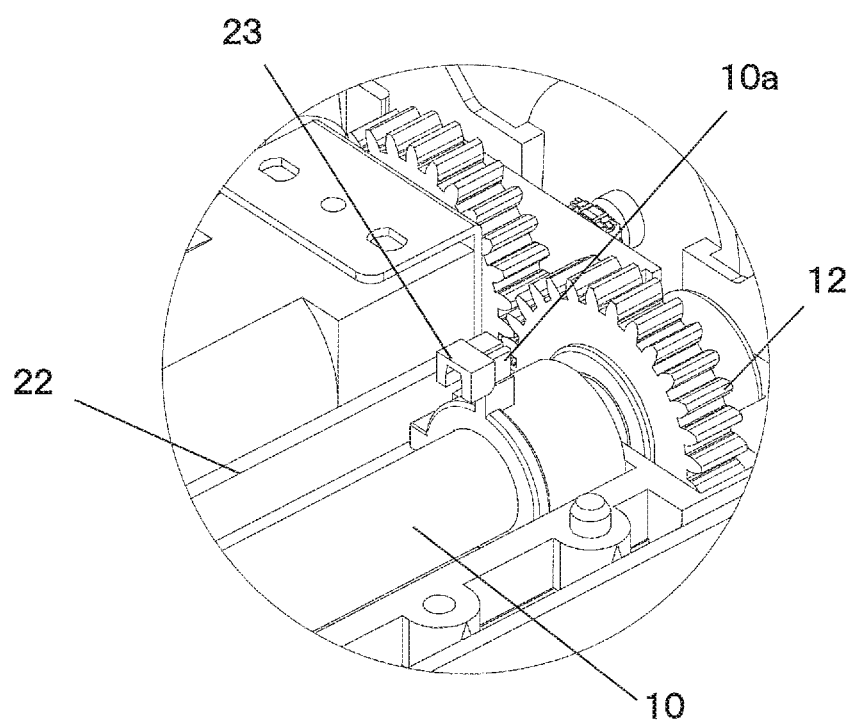
FIG. 13C is an oblique view of the main components of the pharmaceutical injection device shown in FIG. 12.

FIG. 12 is a cross section of the pharmaceutical injection device when the cartridge holder 7 has been opened. FIG. 13A shows the configuration near the origin sensor 23, and is a detail view of the T part in FIG. 12. FIG. 13B is a cross section of near the insertion opening 8 of the cartridge holder 7, and is a detail view of the U part in FIG. 12. FIG. 13C is an oblique view of the configuration near the origin sensor 23.

If the pharmaceutical injection operation is complete in the above-mentioned FIGS. 5, 6A, 6B, 6C, and 11 and there is no more pharmaceutical in the pharmaceutical cartridge 9, the cartridge holder 7 must be opened and the pharmaceutical cartridge 9 replaced.

More specifically, in FIG. 5, for example, when all of the pharmaceutical in the pharmaceutical cartridge 9 has been injected by the piston 10 moving until the gasket of the pharmaceutical cartridge 9 hits the distal end of the pharmaceutical cartridge 9, the piston 10 is retracted by the piston drive mechanism 100 to its origin position, that is, to the position where the piston position information is at zero (see FIG. 4C).

After this, the pharmaceutical cartridge 9 has to be replaced, so the piston 10 is moved upward from the origin position (the pull-out direction D) as shown in FIGS. 13A and 13C.

At this point, since the protrusion 10*b* of the piston 10 and the protrusion 22*b* of the lever 22 are in contact, the lever 22 moves upward (in the pull-out direction D) together.

The ejector finger 20 attached to the lower end of the lever 22 also moves upward together while compressing the biasing spring 21, and this operation disengages the ejector finger 20 and the latched component 19. That is, the contact face 20*a* of the ejector finger 20 slides in the pull-out direction D, and thereby moves away from the contact face 19*a* of the latched component 19.

The cartridge holder 7 at this point is opened outward from the main case 1 (see the arrow A in FIG. 12) by the biasing force of the ejector spring 18, with the axial support component 17 serving as the fulcrum.

Whether or not the cartridge holder 7 has been opened here can be detected by the open/closed detector switch 24 provided near the ejector finger 20 (see FIG. 4B, etc.).

Before this eject operation, the injection needle 16 mounted to the injection needle mounting component 3 must be removed for the sake of safety, so the display component 5 provided to the front of the main case 1 gives a display prompting the user to remove the injection needle 16.

Figure 7:
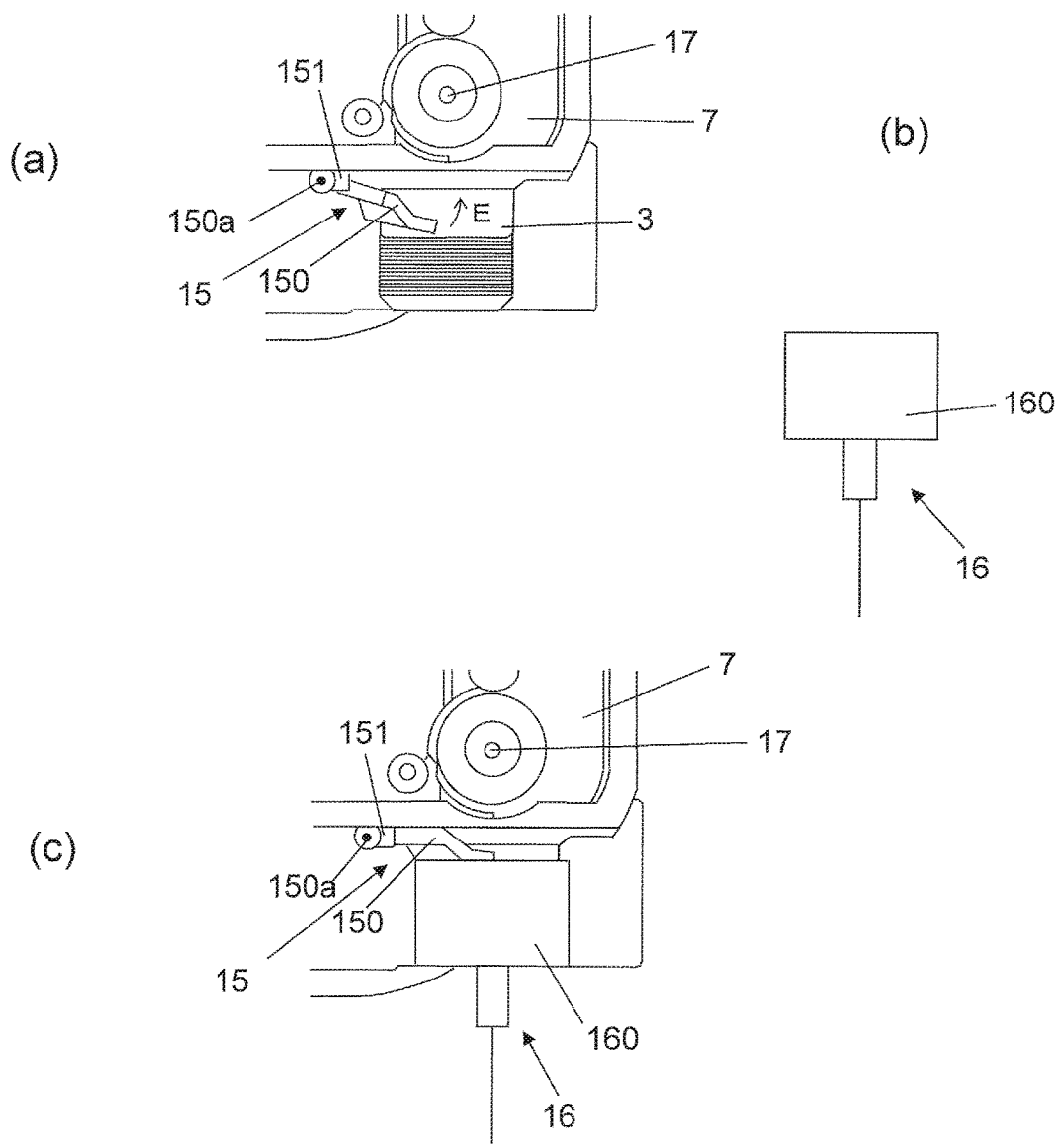
FIG. 7a shows the configuration near an injection needle detector switch in a state in which the injection needle has not been mounted in the pharmaceutical injection device in FIG. 1.
FIG. 7b shows the configuration of the injection needle.
FIG. 7c shows the configuration near the injection needle detector switch in a state in which the injection needle has been mounted in the pharmaceutical injection device in FIG. 1.

The removal of the injection needle 16 can be detected by the needle detector switch 15 shown in FIG. 7.

Next, the operation in which the piston 10 is returned to its origin position will be described through reference to FIGS. 14, 15A, 15B, and 15C.

Figure 14:
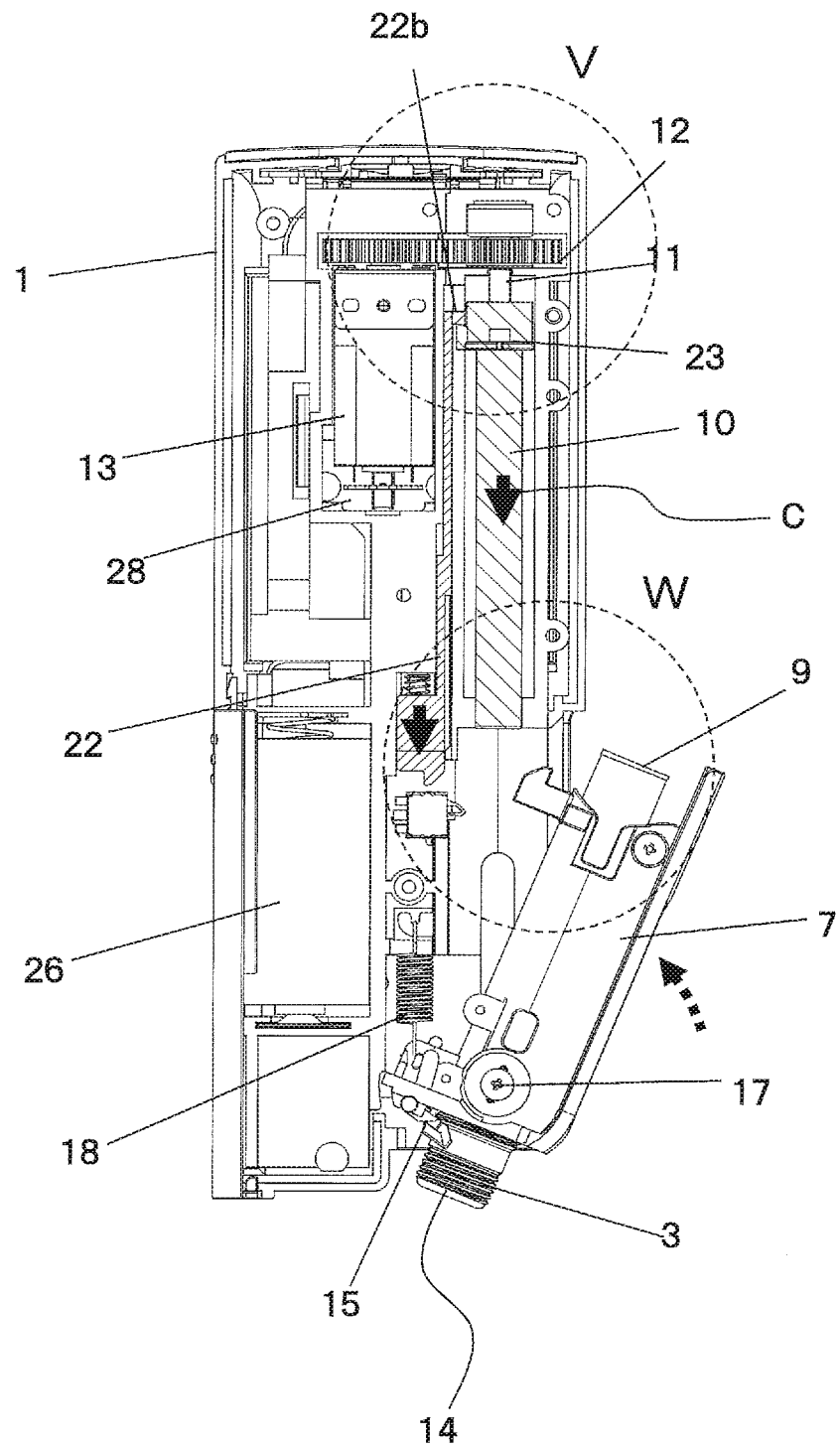
FIG. 14 is a front cross section of the internal configuration of the pharmaceutical injection device shown in FIG. 1.
Figure 15A:
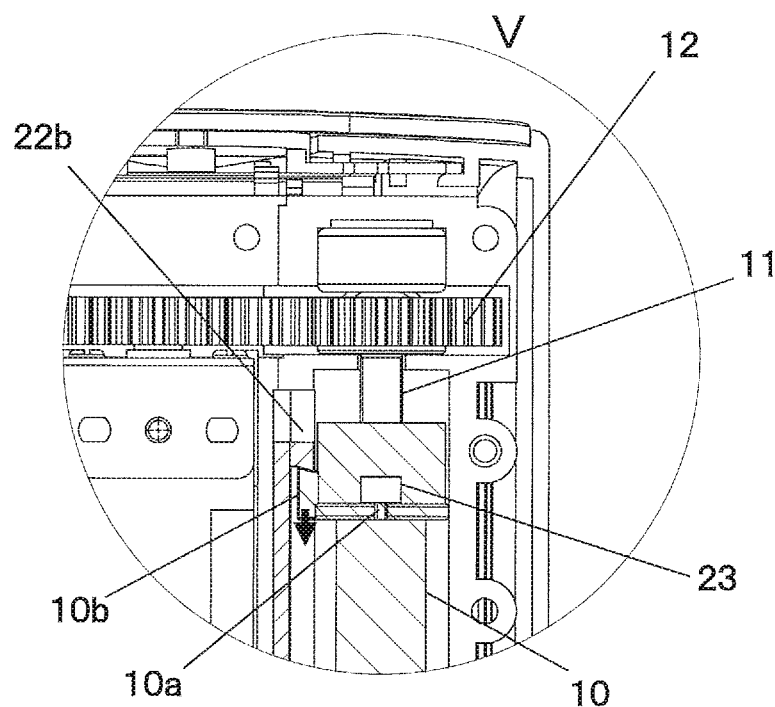
FIG. 15A is a detail view of the main components of the pharmaceutical injection device shown in FIG. 14.
Figure 15B:
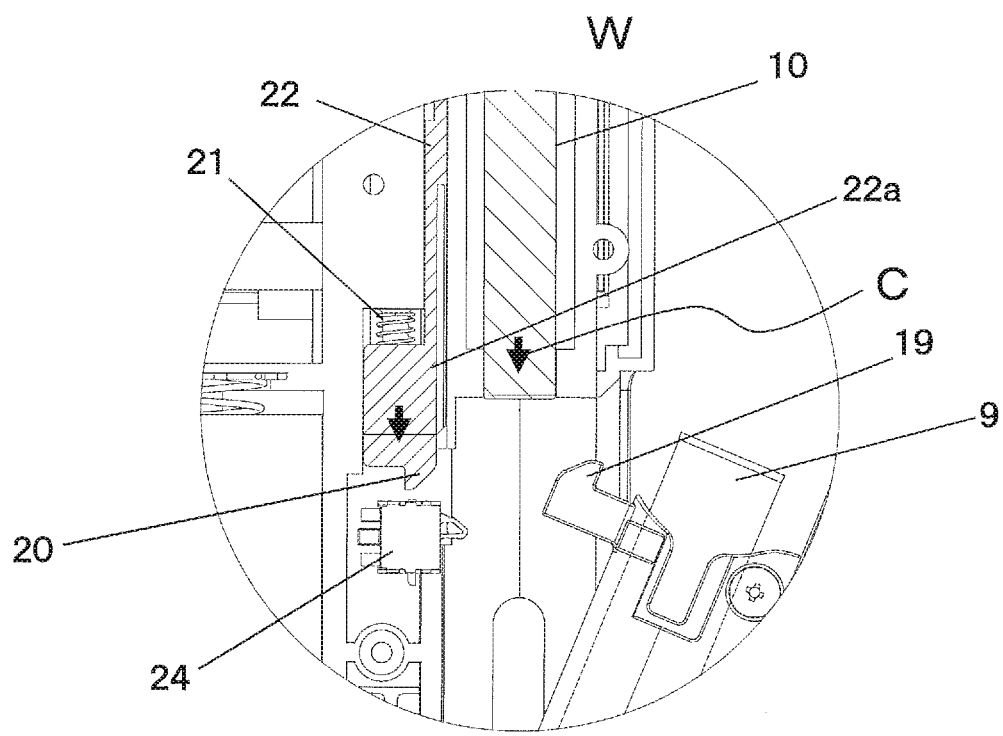
FIG. 15B is a detail view of the main components of the pharmaceutical injection device shown in FIG. 14.
Figure 15C:
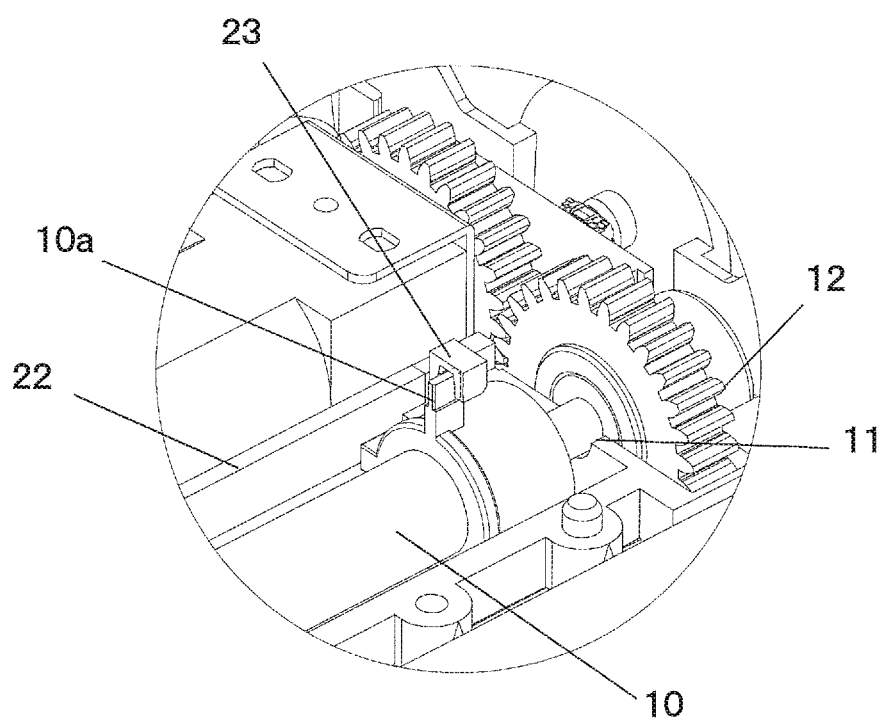
FIG. 15C is an oblique view of the main components of the pharmaceutical injection device shown in FIG. 14.

FIG. 14 is a cross section of the pharmaceutical injection device in a state in which the piston 10 has returned to its origin position while the cartridge holder 7 is open. FIG. 15A shows the configuration near the origin sensor 23, and is a detail view of the V part in FIG. 14. FIG. 15B is a cross section of near the insertion opening 8 of the cartridge holder 7, and is a detail view of the W part in FIG. 14. FIG. 15C is an oblique view of the configuration near the origin sensor 23.

That is, FIGS. 14, 15A, 15B, and 15C show a state in which the piston 10 has been moved in the insertion direction C to its origin position after the eject operation illustrated in FIGS. 12, 13A, 13B, and 13C.

At this pint, the return of the piston 10 to its origin position is accompanied by downward movement of the lever 22 and the ejector finger 20, and a return to the initial state (the position shown in FIG. 3) at the origin position of the piston 10.

Since the cartridge holder 7 at this point is still open, the latched component 19 and the ejector finger 20 are not engaged.

After this, the pharmaceutical cartridge 9 is replaced, and the cartridge holder 7 is moved toward the main case 1 to close it, whereupon the inclined part 19b of the latched component 19 moves while riding up onto the inclined part 20b of the ejector finger 20, and finally the latched component 19 engages with the ejector finger 20 and is held in that state.

That is, upon returning to its initial state and the cartridge holder 7 housing the replaced pharmaceutical cartridge 9 is held inside the main case 1.

Next, the operation in pharmaceutical replacement processing, including the cartridge holder opening operation, will be described on the basis of the flowchart in FIG. 16.

Figure 16:
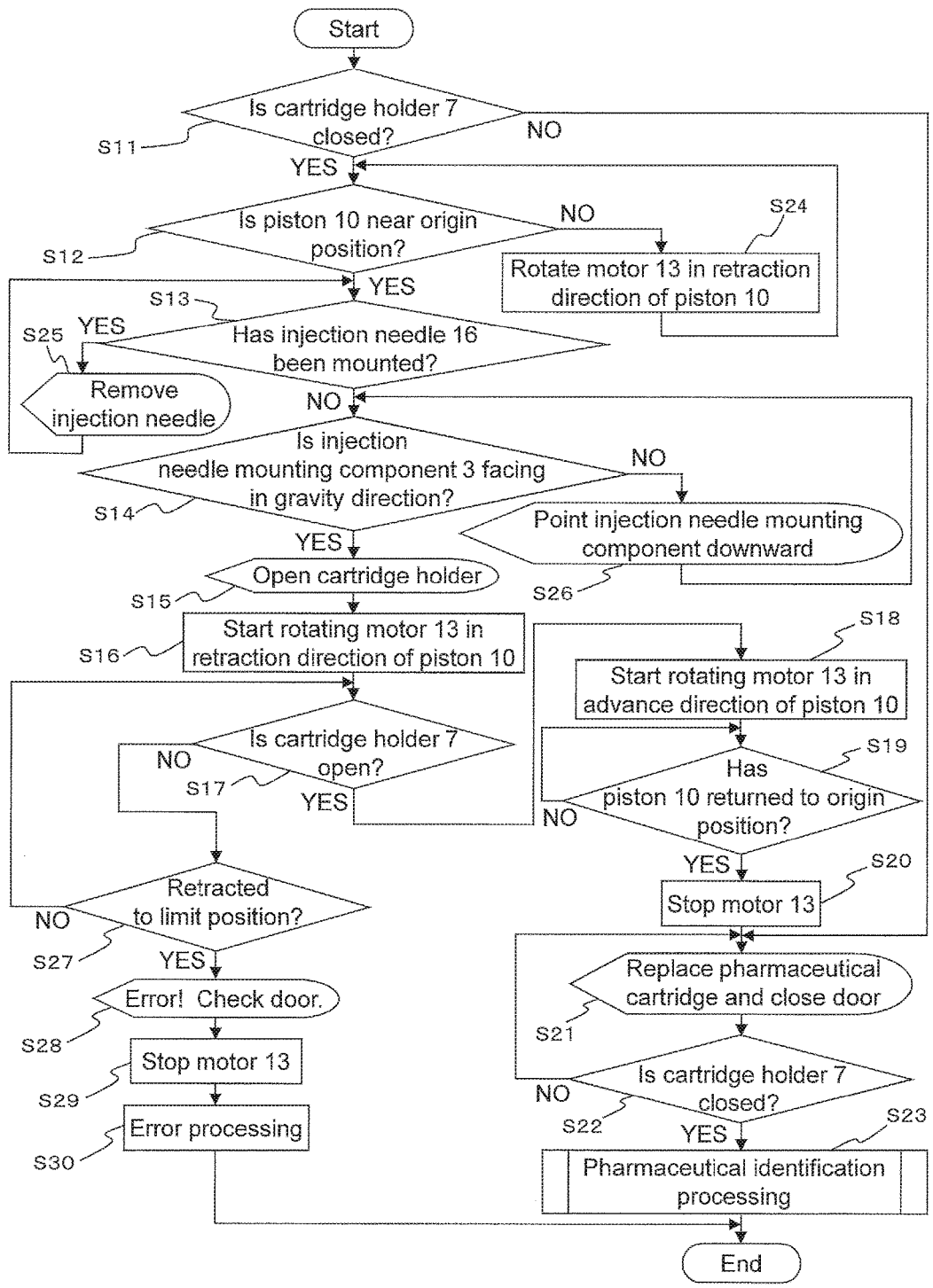
FIG. 16 is a flowchart of pharmaceutical replacement processing in the pharmaceutical injection device in FIG. 1.

FIG. 16 is premised on the timing at which it becomes necessary to eject (open) the cartridge holder 7. Examples of the timing of this ejection (opening) include a case in which the pharmaceutical in the pharmaceutical cartridge 9 has been completely injected as shown in FIG. 9 (S2), a case in which it becomes necessary to replace the pharmaceutical after a specific length of time has elapsed (S3), and a case in which manual replacement has been selected (S4).

A case in which it becomes necessary to replace the pharmaceutical after a specific length of time has elapsed is, for example, one in which more than a specific time period (five weeks in this case) has elapsed since the pharmaceutical cartridge 9 was installed in the pharmaceutical injection device, when the expiration period has been determined to be five weeks after the start of usage.

In this case, if the timer 33 is started when the pharmaceutical cartridge 9 is replaced, and the time on the timer 33 indicates that a specific length of time has elapsed, control is performed so that the pharmaceutical cartridge will be replaced, as an expiration error.

Examples of when the timer 33 is started here include when the pharmaceutical cartridge 9 is replaced and the timer is started at the point when the open/closed detector switch 24 detects that the cartridge holder 7 has been closed, and when the timer is started at the point when the pharmaceutical in the pharmaceutical cartridge 9 was first injected (start of pharmaceutical administration).

Thus, the conditions that require the replacement of the pharmaceutical cartridge 9 include when there is no pharmaceutical in the pharmaceutical cartridge 9, when the pharmaceutical is past its expiration date, and when replacement has been selected from the menu. As discussed above, when it becomes necessary to replace the pharmaceutical cartridge 9, the controller 25 uses the open/closed detector switch 24 to detect whether or not the cartridge holder 7 is closed, as shown in FIG. 16 (S11).

If the cartridge holder 7 is open, the controller 25 displays on the LCD panel (the display component 5) a message prompting the user to replace the pharmaceutical cartridge 9 and close the cartridge holder 7 (displayed as "Door" on the display component 5) (S21).

On the other hand, if the cartridge holder 7 is closed, the controller 25 confirms whether or not the piston 10 is near the origin position by referring to the piston position information stored in the memory 32 (S12).

At this point the controller 25 determines that the piston 10 is near the origin position if the piston position information is zero or within a specific range of positive or negative offset.

If the piston 10 is not near the origin position, the controller 25 actuates the motor control circuit 27, rotates the motor 13, and moves the piston 10 back (in the pull-out direction D) (S24).

If the rotation of the motor 13 in S24 results in the piston position information being zero, it is concluded that the piston 10 has returned to the origin position, and the flow moves from S12 to S13. The motor 13 is stopped at this point.

If the checking of piston position information in S12 reveals that the piston 10 is near the origin position, or if the piston 10 has returned to the origin position in S24, the controller 25 uses the needle detector switch 15 to confirm whether or not the injection needle 16 is mounted (S13). If the injection needle 16 is still mounted, the controller 25 displays on the display component 5 a message prompting the user to remove the injection needle 16 (S25).

If it is confirmed that the injection needle 16 has been removed, the controller 25 uses the acceleration sensor 34 to check whether or not the injection needle mounting component 3 is facing in the gravity direction (S14). If the injection needle mounting component 3 is not facing in the gravity direction, the controller 25 displays "Point injection needle mounting component downward" on the display component 5 (S26). This is because if the opening side of the cartridge holder 7 (the opposite side from the axial support component 17) is facing downward (in the gravity direction), there is the risk that the pharmaceutical cartridge 9 will fall out and be damaged when the cartridge holder 7 is opened. Before the opening operation is performed, the orientation of the device is sensed by the acceleration sensor 34, and if the opening side of the cartridge holder 7 is facing downward, a warning prompting the user to change the orientation of the device is displayed on the display component 5. The device need not be strictly facing in the gravity direction, and it may be considered to be facing in the gravity direction if it is closer to the gravity direction than to the horizontal direction, for example.

Meanwhile, if the injection needle mounting component 3 is facing in the gravity direction, the controller 25 displays on the display component 5 a message telling the user to open the cartridge holder 7 (S15). The rotation of the motor 13 has been stopped at this point.

Thus, no opening operation is performed if the device is not facing in a direction in which the pharmaceutical cartridge 9 will not accidentally fall out when the cartridge holder 7 is opened.

Next, the operation to actually open the cartridge holder 7 is performed (S16).

More specifically, the controller 25 commands the motor control circuit 27 to rotate the motor 13 and move the piston 10 further back (pull-out direction D) from the origin position.

As shown in FIG. 13A, this causes the protrusion 10b of the piston 10 and the protrusion 22b of the lever 22 to come into contact, and the entire slender lever 22 moves upward. Along with this, the ejector finger 20 attached adjacent to the lower side of the lever 22 also retracts upward, moving away and disengaging from the latched component 19 provided to the cartridge holder 7.

As shown in FIG. 13B, when the latched component 19 and the ejector finger 20 are disengaged, the biasing force of the ejector spring 18 causes the cartridge holder 7 to open outward around the axial support component 17.

The controller 25 uses the open/closed detector switch 24 to check whether or not the cartridge holder 7 has opened (S17).

If the cartridge holder 7 has not opened, the controller 25 determines whether or not the current position of the piston 10, found from the output of the encoder 28 connected to the motor 13, has reached a preset limit position (a position at which the piston 10 has retracted far enough from the origin position for the latched component 19 and the ejector finger 20 to separate) (S27).

If the limit position has not been reached, the retraction of the piston 10 is continued. Here, even if the piston 10 has retracted to the limit position, if the open/closed detector switch 24 has not detected the opening of the cartridge holder 7, the controller 25 will display on the display component 5 a warning prompting the user to check the state of the door (the cartridge holder 7) (S28), and will halt the motor 13 (S29). The buzzer 30 may also be sounded simultaneously with the warning display. After this, error processing (S30) is performed and control is ended. In this error processing in S30, the same operations as in S18, S19, and S20 are performed, and the piston 10 returns to its origin position.

Next, if the cartridge holder 7 is open, the controller 25 again moves the piston 10 in the insertion direction C to its origin position via the motor control circuit 27, the motor 13, the gear 12, the feed screw 11, etc. (S18).

The controller 25 then uses the piston position information to confirm whether or not the piston 10 has returned to its origin position (S19), and if it has not returned to the origin position, the operation to advance the piston 10 is continued.

If the piston 10 has returned to its origin position, the controller 25 stops the motor 13 via the motor control circuit 27, and stops the piston 10 (S20).

Next, the controller 25 displays on the display component 5 a message prompting the user to close the cartridge holder 7 after replacement of the pharmaceutical cartridge 9 (S21).

The pharmaceutical cartridge 9 is then replaced, and the open/closed detector switch 24 detects whether or not the cartridge holder 7 has been closed (S22).

If the cartridge holder 7 is still open, the flow returns to S21 and the system waits until it is closed.

If it has been confirmed that the cartridge holder 7 is closed, the controller 25 performs pharmaceutical identification processing (S23). In this pharmaceutical identification processing, the controller 25 uses the identification component 35 to read the identification label 9a affixed to the pharmaceutical cartridge 9, and confirms whether or not the proper pharmaceutical cartridge 9 has been mounted to the cartridge holder 7. If it is determined that an improper pharmaceutical cartridge 9 has been mounted to the cartridge holder 7, the controller 25 gives an error display on the display component 5, and performs control to open the cartridge holder 7. On the other hand, if the controller 25 determines that the proper pharmaceutical cartridge 9 has been mounted to the cartridge holder 7, pharmaceutical replacement processing is ended. The timer 33 (see FIG. 11) may be started at this point.

3. Main Features

1

The pharmaceutical injection device in the above embodiment comprises the cartridge holder 7, the main case 1, the piston 10, the piston drive mechanism 100, the opening component 130, the open/closed detector switch 24, and the controller 25. The pharmaceutical cartridge 9 is mounted to the cartridge holder 7. The cartridge holder 7 is provided openably and closeably to the main case 1. The piston can be inserted into the pharmaceutical cartridge 9 mounted to the cartridge holder 7. The piston drive mechanism 100 drives the piston 10 to move in either the insertion direction C in which the piston 10 is inserted into the pharmaceutical cartridge 9 or the pull-out direction D in which the piston 10 is pulled out of the pharmaceutical cartridge 9. The opening component 130 opens the cartridge holder 7 in conjunction with the movement of the piston 10 in the pull-out direction D. the open/closed detector switch 24 detects whether the cartridge holder 7 is open or closed. The controller 25 controls the piston drive mechanism 100 so as to stop the piston 10 when the open/closed detector switch 24 has detected that the cartridge holder 7 is open.

Since the cartridge holder is thus opened in conjunction with movement of the piston 10 in the pull-out direction D, the user can easily replace the pharmaceutical cartridge without having to operate an eject button or the like.

2

With the pharmaceutical injection device in the above embodiment, an origin position (an example of a reference position) at which the cartridge holder 7 can be kept closed in a state in which the pharmaceutical cartridge 9 has not yet been inserted, is provided as the position where the piston 10 moves. The opening component 130 opens the cartridge holder 7 in conjunction with movement of the piston 10 in the pull-out direction D from the origin position (an example of a reference position).

The piston 10 can be located at the origin position at which the cartridge holder 7 can be kept closed in a state in which the pharmaceutical cartridge 9 has not yet been inserted, and when the piston 10 has moved in the pull-out direction D from the origin position, the cartridge holder 7 is opened. Thus, the cartridge holder 7 can be opened only when the pharmaceutical cartridge 9 needs to be replaced, so it is less likely that it will be opened unintentionally by the user.

3

Also, with the pharmaceutical injection device in this embodiment, the opening component 130 has the protrusion 22b, the ejector finger 20, the lever 22, and the ejector spring 18. The protrusion 22b hits the protrusion 10b formed on the piston 10 when the piston 10 moves in the pull-out direction D from its origin position, and moves in the pull-out direction D along with movement of the piston 10. The ejector finger 20 latches the latched component 19 formed on the cartridge holder 7. The lever 22 links the protrusion 22b and the ejector finger 20. The ejector spring 18 biases the cartridge holder 7 in its opening direction. As the protrusion 10b moves in the pull-out direction D, the ejector finger 20 operates via the lever 22 to release the latching of the latched component 19 by the ejector finger 20, and the cartridge holder 7 is opened by the biasing force of the ejector spring 18.

With this configuration, when the pharmaceutical cartridge 9 needs to be replaced, for example, the ejector finger 20 is moved away from the latched component 19 of the cartridge holder 7 by the piston 10 or the motor 13, and in this state the cartridge holder 7 is moved in the opening direction from the main case 1 by the ejector spring 18, that is, the cartridge holder is opened automatically, which makes the device extremely convenient to use.

4

Also, in this embodiment, the protrusion 22b, the lever 22, and the ejector finger 20 are disposed along the movement direction of the piston 10. The pharmaceutical injection device in this embodiment comprises the spring 21 for biasing the protrusion 22b, the lever 22, and the ejector finger 20 in the insertion direction C. The spring 21 biases the ejector finger 20 so as to latch the latched component 19, and when the piston 10 moves in the pull-out direction D from its origin position, the protrusion 22b, the lever 22, and the ejector finger 20 are moved backward by the biasing force of the spring 21, and the latching of the latched component 19 by the ejector finger 20 is released.

Thus providing the spring 21 allows the latched component 19 to be latched by the ejector finger 20 merely by closing the cartridge holder 7, so the cartridge holder 7 can be kept closed.

4. Other Embodiments

A

As shown in FIG. 9, in the above embodiment, when the power is turned on (S1), the pharmaceutical cartridge 9 is replaced if there is no more pharmaceutical remaining (S2), if the expiration date is past (S3), or if manual replacement is selected (S4), but replacement is not limited to these situations.

For instance, the pharmaceutical replacement processing (S4) may be performed if the remaining amount of pharmaceutical is less than the amount that is supposed to be injected the next time, after pharmaceutical injection processing (S7), after the remaining amount of pharmaceutical is shown in S8, and before the power is turned off.

B

In the above embodiment, in S27, it was determined to stop the motor 13 depending on whether or not the current position of the piston 10 found from the output of the encoder 28 has moved to the limit position, but the timer 33 may be used instead of using the output from the encoder 28. That is, when the timer 33 is used, the count of the timer 33 is started after rotating the motor 13 in S16, and control is performed to stop the motor 13 if it has not been detected that the cartridge holder 7 is open even after the elapse of the time it takes for the piston 10 to move in the pull-out direction D far enough for the latched component 19 and the ejector finger 20 to separate.

C

C-1

Figure 17:
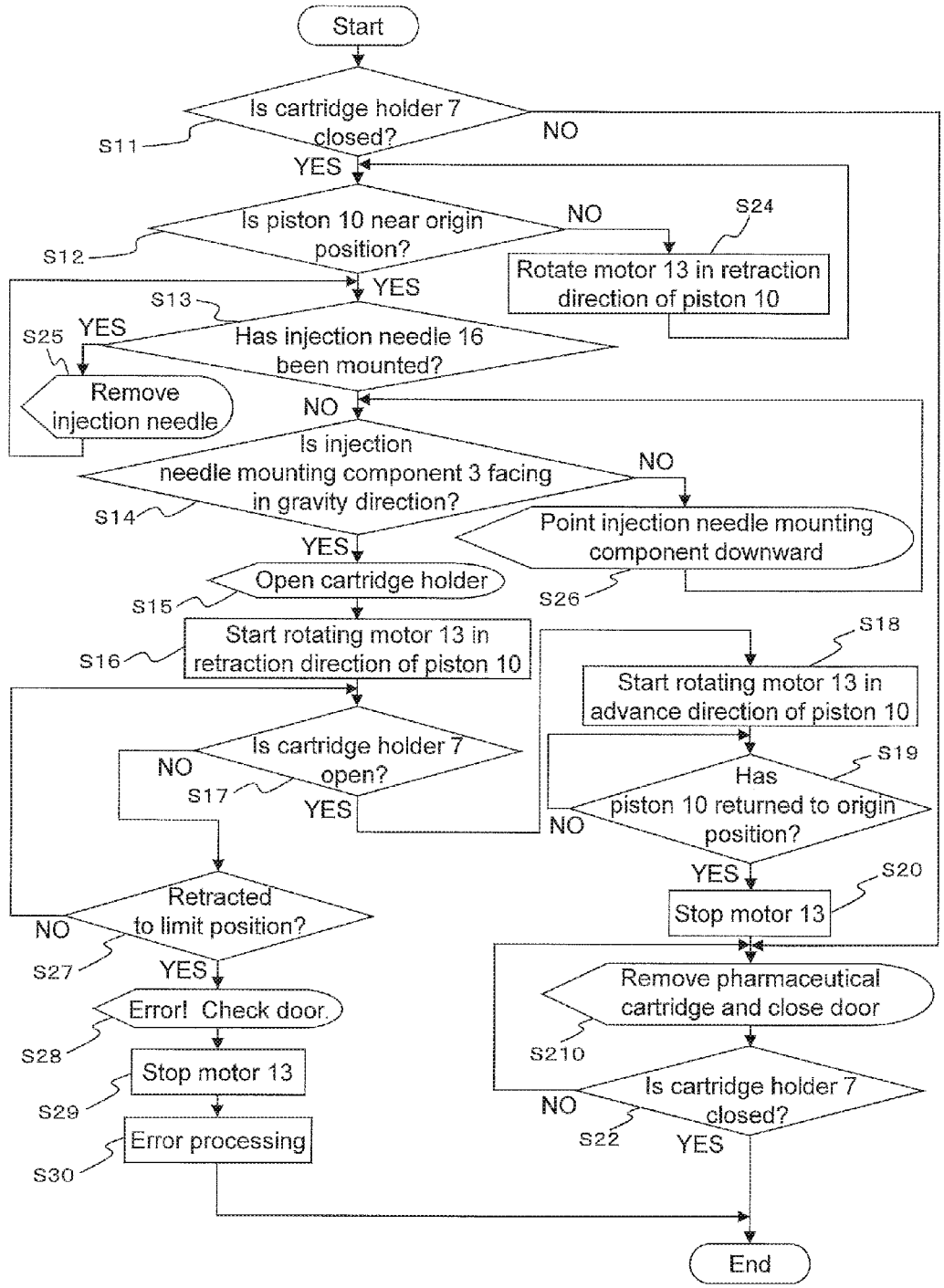
FIG. 17 is a flowchart of pharmaceutical replacement processing in the pharmaceutical injection device in a modification example of an embodiment pertaining to the present invention.

In the above embodiment, operation is described in which the cartridge holder 7 is opened for pharmaceutical replacement, but the pharmaceutical cartridge 9 may just be taken out, without being replaced. For instance, an operation to open the cartridge holder 7 is performed when the user selects the door (cartridge holder 7) opening menu displayed on the display component 5. FIG. 17 is a flowchart of cartridge opening processing. The flowchart shown in FIG. 17 differs from the flowchart shown in FIG. 16 in that S210 is provided instead of S21. In S210, a message of "Close cartridge holder" is displayed on the display component 5. Since no pharmaceutical cartridge 9 is mounted, S23 in FIG. 16 is not provided in the flowchart shown in FIG. 17.

Also, if a pharmaceutical cartridge 9 that needs to be refrigerated is used, the operation to open the cartridge holder 7 when the pharmaceutical cartridge 9 is removed may be executed after the pharmaceutical injection processing (S7).

C-2

Also, in FIG. 9, the control in S2, S3, S4, and S5 is premised on a state in which the pharmaceutical cartridge 9 is mounted in the cartridge holder 7, but when a pharmaceutical cartridge 9 that needs to be refrigerated is used, the operation to open the cartridge holder 7 is performed after the power is turned on (S1). This opening operation is the same as the operation shown in FIG. 17, but the pharmaceutical identification operation shown in FIG. 16 (S23) is performed after the display in S210.

As discussed above, the operation to open the cartridge holder 7 is performed not only when the pharmaceutical cartridge is replaced, but also when the pharmaceutical cartridge is removed, when the pharmaceutical cartridge is mounted, and so forth.

D

In the above embodiment, a configuration is described in which the movement of the piston 10 acts on the lever 22 to open the cartridge holder 7, but a solenoid may be used instead, for example. This will be described through reference to FIGS. 18 to 20.

Figure 18:
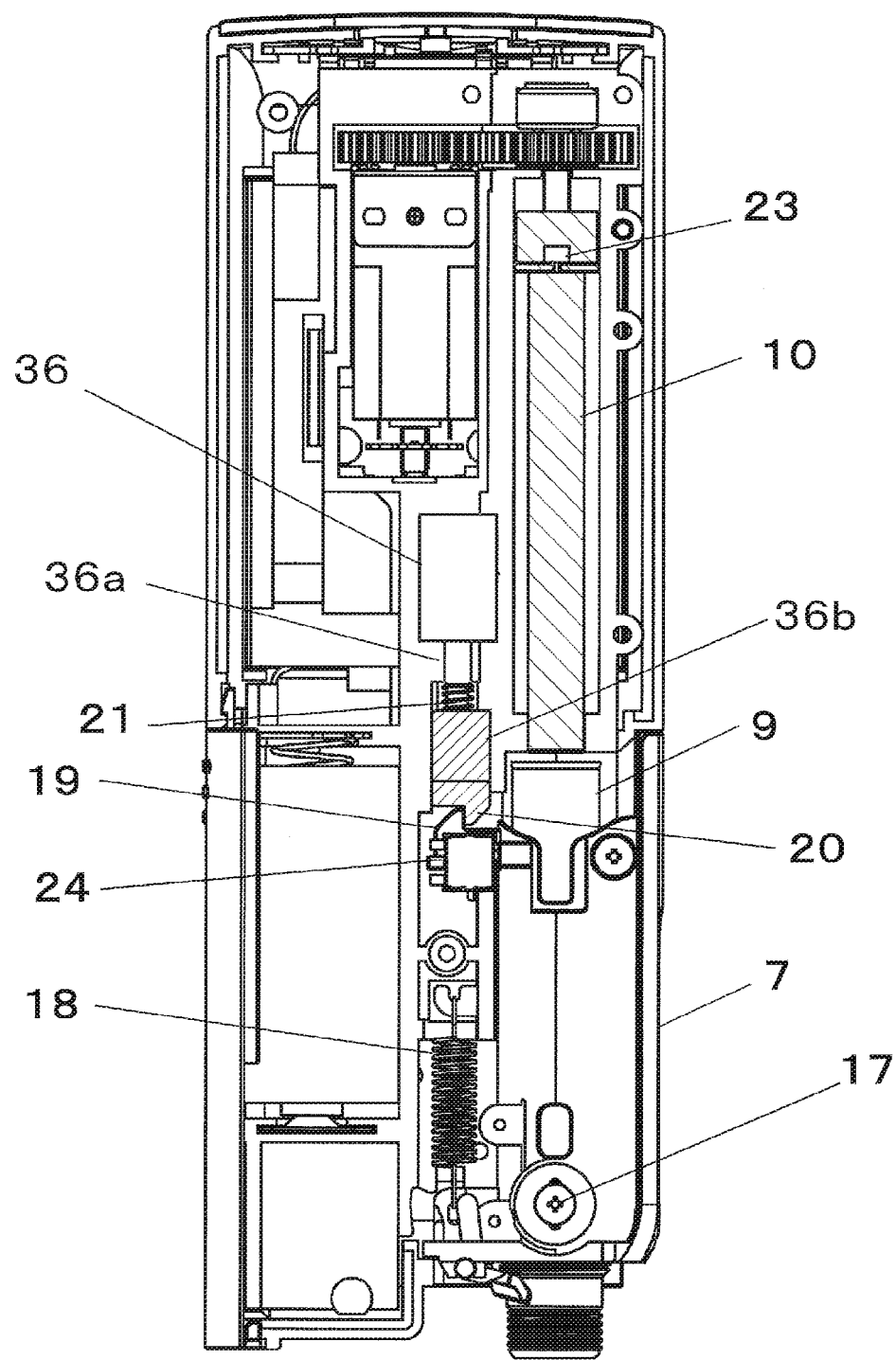
FIG. 18 is a front cross section of the internal configuration of the pharmaceutical injection device in a modification example of an embodiment pertaining to the present invention.

FIG. 18 is a front cross section of the internal configuration of the pharmaceutical injection device, and shows a modification of what is shown in FIG. 3. The pharmaceutical injection device shown in FIG. 18 differs from the pharmaceutical injection device shown in FIG. 3 in that a solenoid 36 is provided, and that a linking component 36b is provided instead of the lever 22. The linking component 36b links the ejector finger 20 to a movable core 36a, which is an element of the solenoid 36. The movable core 36a is linked to the linking component 36b through the inside of the spring 21. One end of the spring 21 touches the main case 1, the other end touches the linking component 36b, and the spring 21 is disposed so as to bias the linking component 36b downward. Specifically, just as with the action of the lever 22 shown in FIG. 3, the action of the solenoid 36 causes the ejector finger 20 linked to the linking component 36b to move up or down.

Figure 19:
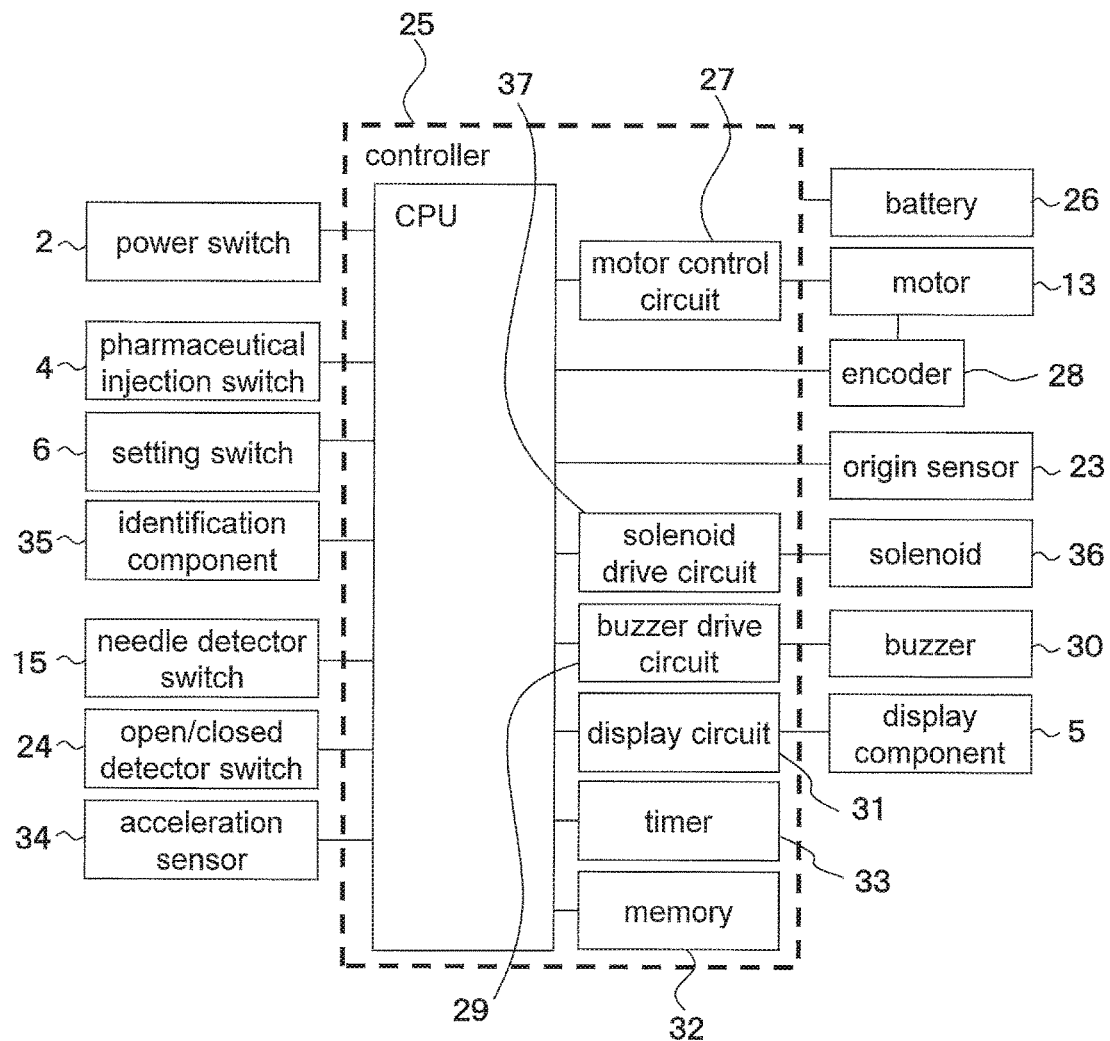
FIG. 19 is a block diagram of the control configuration of the pharmaceutical injection device in a modification example of an embodiment pertaining to the present invention.

FIG. 19 is a block diagram of the control configuration of the pharmaceutical injection device, and shows a modification of what is shown in FIG. 8. The block diagram in FIG. 19 differs from the block diagram in FIG. 8 in that the controller 25 has a solenoid drive circuit 37 for driving the solenoid 36, and this solenoid drive circuit 37 is connected to the CPU 250.

The operation in pharmaceutical replacement processing, including the operation to open the cartridge holder 7, with a configuration featuring the solenoid 36 will now be described through reference to the flowchart in FIG. 20.

Figure 20:
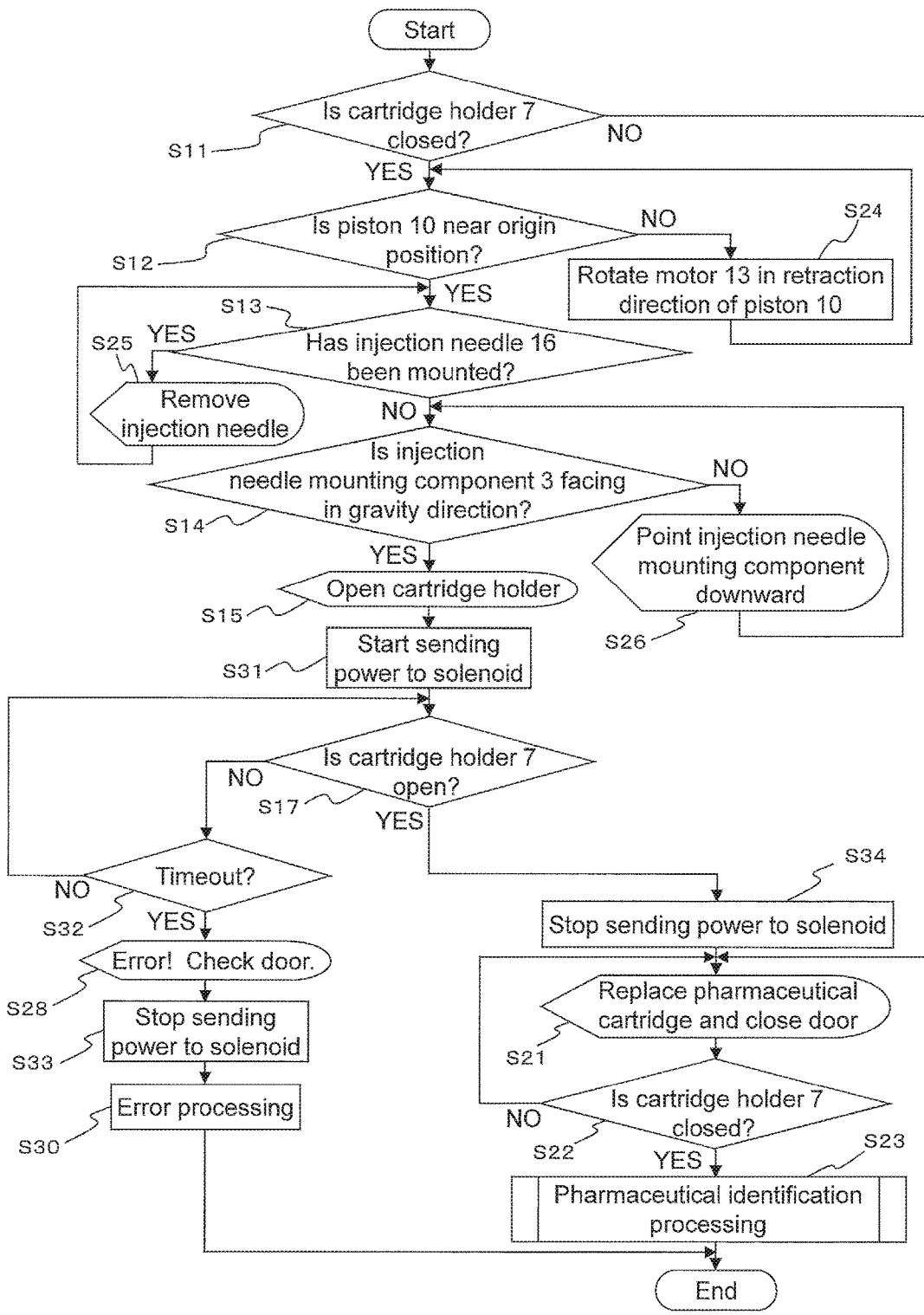
FIG. 20 is a flowchart of pharmaceutical replacement processing in the pharmaceutical injection device in a modification example of an embodiment pertaining to the present invention.

As shown in FIG. 20, when the pharmaceutical cartridge 9 needs to be replaced, the controller 25 uses the open/closed detector switch 24 to detect whether or not the cartridge holder 7 is closed (S11).

If the cartridge holder 7 is open at this point, a message prompting the user to replace the pharmaceutical cartridge 9 and close the cartridge holder 7 (displayed as "Door" on the display component 5) is displayed on the LCD panel (the display component 5) (S21).

On the other hand, if the cartridge holder 7 is closed, the controller 25 refers to the piston position information stored in the memory 32 to determine whether or not the piston 10 is near the origin position (S12).

At this point, the controller 25 determines that the piston 10 is near the origin position if the piston position information is zero or within a specific range of positive or negative offset.

If the piston 10 is not near the origin position, the controller 25 actuates the motor control circuit 27, rotates the motor 13, and moves the piston 10 back (in the pull-out direction D) (S24).

If the rotation of the motor 13 in S24 results in the piston position information being zero, it is concluded that the piston 10 has returned to the origin position, and the flow moves from S12 to S13. The motor 13 is stopped at this point.

If the checking of piston position information in S12 reveals that the piston 10 is near the origin position, or if the piston 10 has returned to the origin position in S24, the controller 25 uses the needle detector switch 15 to confirm whether or not the injection needle 16 is mounted (S13). If the injection needle 16 is still mounted, the controller 25 displays on the display component 5 a message prompting the user to remove the injection needle 16 (S25).

If it is confirmed that the injection needle 16 has been removed, the controller 25 uses the acceleration sensor 34 to check whether or not the injection needle mounting component 3 is facing in the gravity direction (S14). If the injection needle mounting component 3 is not facing in the gravity direction, the controller 25 displays "Point injection needle mounting component downward" on the display component 5 (S26). This is because if the opening side of the cartridge holder 7 (the opposite side from the axial support component 17) is facing downward (in the gravity direction), there is the risk that the pharmaceutical cartridge 9 will fall out and be damaged when the cartridge holder 7 is opened. Before the opening operation is performed, the orientation of the device is sensed by the acceleration sensor 34, and if the opening side of the cartridge holder 7 is facing downward, a warning prompting the user to change the orientation of the device is displayed on the display component 5. The device need not be strictly facing in the gravity direction, and it may be considered to be facing in the gravity direction if it is closer to the gravity direction than to the horizontal direction, for example.

Meanwhile, if the injection needle mounting component 3 is facing in the gravity direction, the controller 25 displays on the display component 5 a message telling the user to open the cartridge holder 7 (S15). The rotation of the motor 13 has been stopped at this point.

Next, the operation to actually open the cartridge holder 7 is performed.

More specifically, the controller 25 commands the solenoid drive circuit 37 to start sending power to the solenoid 36 (S31). When power is sent to an internal coil (not shown) in the solenoid 36, an attractive force is generated between the movable core 36a and a stationary core (not shown) in the solenoid 36, and the movable core 36a pulls the linking component 36b up. As this happens, the ejector finger 20 attached adjacent to the lower side of the linking component 36b also moves upward and away from the latched component 19 provided to the cartridge holder 7, which releases their engagement.

When the latched component 19 and the ejector finger 20 are disengaged, the biasing force of the ejector spring 18 opens the cartridge holder 7 outward around the axial support component 17.

The controller 25 uses the open/closed detector switch 24 to determine whether or not the cartridge holder 7 has opened (S17).

If the cartridge holder 7 has not opened, the controller 25 uses the timer 33 to determine whether or not the elapsed time since the start of operation of the solenoid 36 has exceeded a timeout time (S32).

If the timeout time has not been exceeded, power continues to be sent to the solenoid 36. Here, even though the length of time since the start of operation of the solenoid 36 has exceeded the timeout time, if the open/closed detector switch 24 does not detect the opening of the cartridge holder 7, the controller 25 causes the display component 5 to display a warning prompting the user to check the state of the door (cartridge holder 7) (S28), and power to the solenoid 36 is shut off (S33). The buzzer 30 may also be sounded simultaneously with the warning display. After this, error processing (S30) is performed and control is ended.

Next, if the cartridge holder 7 is open, the controller 25 shuts off the power to the solenoid 36 (S34). When power to the internal coil of the solenoid 36 is shut off, the attractive force of the stationary core and the movable core 36a is eliminated, and the spring 21 returns the movable core 36a, the linking component 36b, and the ejector finger 20 to their initial positions (the position where the ejector finger 20 can be engaged with the latched component 19 of the cartridge holder 7).

Next, the controller 25 causes the display component 5 to display a message prompting the user to close the cartridge holder 7 after replacing the pharmaceutical cartridge 9 (S21).

The pharmaceutical cartridge 9 is then replaced, and the open/closed detector switch 24 detects whether or not the cartridge holder 7 has been closed (S22).

If the cartridge holder 7 is still open, the flow returns to S21 and the system waits until it is closed.

If it has been confirmed that the cartridge holder 7 is closed, the controller 25 performs pharmaceutical identification processing (S23). In this pharmaceutical identification processing, the controller 25 uses the identification component 35 to read the identification label 9a affixed to the pharmaceutical cartridge 9, and confirms whether or not the proper pharmaceutical cartridge 9 has been mounted to the cartridge holder 7. If it is determined that an improper pharmaceutical cartridge 9 has been mounted to the cartridge holder 7, the controller 25 gives an error display on the display component 5, and performs control to open the cartridge holder 7. On the other hand, if the controller 25 determines that the proper pharmaceutical cartridge 9 has been mounted to the cartridge holder 7, pharmaceutical replacement processing is ended. The timer 33 (see FIG. 11) may be started at this point.

INDUSTRIAL APPLICABILITY

As discussed above, the pharmaceutical injection device of certain embodiments of the present invention allows a cartridge holder to be openly easily, and is expected to find use as a pharmaceutical injection device for injecting insulin, growth hormone, or another such pharmaceutical, for example.

The invention claimed is:

1. A pharmaceutical injection device, comprising:
a cartridge holder to which a pharmaceutical cartridge is mounted;
a main case to which the cartridge holder is provided openably and closeably;
a piston that can be inserted into the pharmaceutical cartridge mounted to the cartridge holder;
a driver that drives the piston to move in either an insertion direction in which the piston is inserted into the pharmaceutical cartridge, or a pull-out direction in which the piston is pulled out of the pharmaceutical cartridge;
an opening component that opens the cartridge holder in conjunction with the movement of the piston in the pull-out direction;
a cartridge holder detector that detects whether the cartridge holder is open or closed;
a controller that controls the driver so as to stop the piston when the cartridge holder detector has detected that the cartridge holder is open;
wherein a reference position, at which the cartridge holder can be held in a closed state when not inserted into the pharmaceutical cartridge, is provided as a position to which the piston moves;
the opening component opens the cartridge holder in conjunction with the movement of the piston in the pull-out direction from the reference position;
the opening component has:
a contacted component that is hit by a contacting component formed on the piston, and moves in the pull-out direction along with movement of the piston when the piston moves from the reference position in the pull-out direction;
a latching component that latches a latched component formed on the cartridge holder;
a linking component that links the contacted component and the latching component; and
a first biasing member that biases the cartridge holder in its opening direction, and
the latching component operates via the linking component along with movement of the latched component in the pull-out direction, which releases the latching of the latched component by the latching component, and the cartridge holder is opened by the biasing force of the first biasing member.

2. The pharmaceutical injection device according to claim 1,
wherein the latched component, the linking component, and the latching component are disposed along the movement direction of the piston,
the device further comprises a second biasing member that biases the latched component, the linking component, and the latching component in the insertion direction,
the second biasing member biases the latching component so as to latch the latched component, and
movement of the piston from the reference position in the pull-out direction causes the latched component, the linking component, and the latching component to move against the biasing force of the second biasing member, and releases the latching of the latched component by the latching component.

3. The pharmaceutical injection device according to claim 1, comprising:
a reference position sensor that senses that the piston is disposed in the reference position; and
a time measurement component that measures elapsed time,
wherein the controller performs control to operate the driver so as to move the piston from the reference position sensor in the pull-out direction, after which the operation of the driver is stopped if the opening of the cartridge holder is not sensed even though a specific amount of time has elapsed.

4. The pharmaceutical injection device according to claim 1, comprising:
a reference position sensor that senses that the piston is disposed in the reference position;
a display component that is provided at the main case; and
a time measurement component that measures elapsed time,
wherein the controller performs control to operate the driver so as to move the piston from the reference position sensor in the pull-out direction, after which a display indicating an error is displayed on the display component if the opening of the cartridge holder is not sensed even though a specific amount of time has elapsed.

5. The pharmaceutical injection device according to claim 1, comprising:
a reference position sensor that senses that the piston is disposed in the reference position; and
a movement amount sensor that senses an amount of movement of the piston on the basis of an output of a motor attached to the driver,
wherein the controller performs control to operate the driver so as to move the piston from the reference position sensor in the pull-out direction, after which the operation of the driver is stopped if the opening of the cartridge holder is not sensed even though the amount of movement of the piston sensed by the movement amount sensor has reached a specific amount of movement.

6. The pharmaceutical injection device according to claim 1, comprising:
a reference position sensor that senses that the piston is disposed in the reference position; and
a movement amount sensor that senses an amount of movement of the piston on the basis of the output of a motor attached to the driver,
wherein the controller operates the driver so as to move the piston from the reference position sensor in the pull-out direction, after which a display indicating an error is displayed on a display component if the opening of the cartridge holder is not sensed even though the amount of movement of the piston sensed by the movement amount sensor has reached a specific amount of movement.

7. The pharmaceutical injection device according to claim 1, wherein the cartridge holder is tubular in shape, with an insertion opening into which the pharmaceutical cartridge is inserted provided at the end on the pull-out direction side, and has:
an axial support component that is provided at an outer surface of the main case at the end of the cartridge holder on the insertion direction side, and that rotatably supports the cartridge holder on the main case; and
a holder-side linking component that is provided opposite the axial support component at the end of the cartridge holder on the insertion direction side, and to which is linked a first end of the first biasing member,
wherein the main case has a main body-side linking component to which is linked a second end of the first biasing member disposed along the cartridge holder, and
the first biasing member biases so as to pull the holder-side linking component to the main body-side linking component.

8. A pharmaceutical injection device, comprising:
a cartridge holder to which a pharmaceutical cartridge is mounted;
a main case to which the cartridge holder is provided openably and closeably;
a piston that can be inserted into the pharmaceutical cartridge mounted to the cartridge holder;
a driver that drives the piston to move in either an insertion direction in which the piston is inserted into the pharmaceutical cartridge, or a pull-out direction in which the piston is pulled out of the pharmaceutical cartridge;
an opening component that opens the cartridge holder in conjunction with the movement of the piston in the pull-out direction;
a cartridge holder detector that detects whether the cartridge holder is open or closed;
a controller that controls the driver so as to stop the piston when the cartridge holder detector has detected that the cartridge holder is open; and
a time measurement component that measures elapsed time since the pharmaceutical cartridge was mounted to the cartridge holder,
wherein the controller moves the piston in the pull-out direction so as to operate the opening component if the elapsed time has reached a specific length of time.

9. The pharmaceutical injection device according to claim 8, comprising a display component that is provided at the main case,
wherein the controller displays on the display component a display to give notice of the opening of the cartridge holder, before the cartridge holder is opened.

10. The pharmaceutical injection device according to claim 8, comprising a display component that is provided at the main case,
wherein the controller displays on the display component a display that prompts a user to replace the pharmaceutical cartridge when the opening of the cartridge holder is sensed by the cartridge holder detector.

11. The pharmaceutical injection device according to claim 10, wherein the controller displays on the display component a display that prompts a user to replace the pharmaceutical cartridge and then to close the cartridge holder when the opening of the cartridge holder is sensed by the cartridge holder detector.

12. The pharmaceutical injection device according to claim 8 and further,
comprising a reader that reads an identification component provided on the pharmaceutical cartridge,
wherein, when the cartridge holder detector detects that the cartridge holder has been closed after the display, the controller uses the reader to read the identification component and determines whether or not a proper pharmaceutical cartridge has been mounted.

13. A pharmaceutical injection device, comprising:
a cartridge holder to which a pharmaceutical cartridge is mounted;
a main case to which the cartridge holder is provided openably and closeably;
a piston that can be inserted into the pharmaceutical cartridge mounted to the cartridge holder;
a driver that drives the piston to move in either an insertion direction in which the piston is inserted into the pharmaceutical cartridge, or a pull-out direction in which the piston is pulled out of the pharmaceutical cartridge;
an opening component that opens the cartridge holder in conjunction with the movement of the piston in the pull-out direction;
a cartridge holder detector that detects whether the cartridge holder is open or closed;
a controller that controls the driver so as to stop the piston when the cartridge holder detector has detected that the cartridge holder is open;
an injection needle mounting component for mounting an injection needle that injects a pharmaceutical from the pharmaceutical cartridge into a body;
an injection needle detector that detects the mounting of the injection needle to the injection needle mounting component; and
a display component that is provided at the main case,
wherein the controller displays on a display component a display prompting the user to remove the injection needle prior to the opening of the cartridge holder when the injection needle detector has detected the mounting of the injection needle.

14. A pharmaceutical injection device, comprising:
a cartridge holder to which a pharmaceutical cartridge is mounted;
an openable and closeable main case attached to the cartridge holder;
a piston that can be inserted into the pharmaceutical cartridge mounted to the cartridge holder;
a driver that drives the piston to move in either an insertion direction in which the piston is inserted into the pharmaceutical cartridge, or a pull-out direction in which the piston is pulled out of the pharmaceutical cartridge;
an opening component that opens the cartridge holder in conjunction with the movement of the piston in the pull-out direction;
an orientation sensor that senses an orientation of the main case; and
a controller that operates the opening component to open the cartridge holder when the orientation sensor has sensed that the main case is in a specific orientation.

15. The pharmaceutical injection device according to claim 14,
wherein the specific orientation is an orientation in which the pharmaceutical cartridge can be maintained in a state of being disposed inside the cartridge holder without falling out, when the cartridge holder has been opened.

16. The pharmaceutical injection device according to claim 14, further
comprising an injection needle mounting component attached to the cartridge holder for mounting an injection needle,
wherein the specific orientation is an orientation in which the injection needle mounting component is facing in the gravity direction.

* * * * *